(12) United States Patent
Gosselin et al.

(10) Patent No.: US 6,458,773 B1
(45) Date of Patent: Oct. 1, 2002

(54) NUCLEOSIDE WITH ANTI-HEPATITIS B VIRUS ACTIVITY

(75) Inventors: Gilles Gosselin, Montpellier (FR); Jean-Louis Imbach, Montpellier (FR); Jean-Pierre Sommadossi, Birmingham, AL (US); Raymond F. Schinazi, Decatur, GA (US)

(73) Assignees: Emory University, Atlanta, GA (US); Centre National de la Recherche Scientifique, Paris (FR); UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/435,261

(22) Filed: Nov. 5, 1999

Related U.S. Application Data

(60) Provisional application No. 60/107,116, filed on Nov. 5, 1998, and provisional application No. 60/115,653, filed on Jan. 13, 1999, now abandoned.

(51) Int. Cl.⁷ ..................... A61K 31/70; C07H 19/067; C07H 19/073; C07H 19/10
(52) U.S. Cl. ..................... 514/49; 514/51; 536/26.8; 536/28.52; 536/28.2
(58) Field of Search ................ 514/49, 51; 536/26.8, 536/28.52, 28.2

(56) References Cited

U.S. PATENT DOCUMENTS

| | | |
|---|---|---|
| 4,681,933 A | 7/1987 | Chu et al. |
| 4,841,039 A | 6/1989 | Chu et al. |
| 4,916,122 A | 4/1990 | Chu et al. |
| 5,041,449 A | 8/1991 | Belleau et al. ............ 514/274 |
| 5,047,407 A | 9/1991 | Belleau et al. ............ 514/274 |
| 5,077,279 A | 12/1991 | Chu et al. |
| 5,084,445 A | 1/1992 | Chu et al. |
| 5,190,926 A | 3/1993 | Chu et al. |
| 5,539,116 A | 7/1996 | Liotta et al. ............ 514/317 |
| 5,703,058 A | 12/1997 | Schinazi et al. ............ 514/45 |

FOREIGN PATENT DOCUMENTS

| | | |
|---|---|---|
| DE | 42 24 737 | 3/1994 |
| EP | 0 337 713 | 10/1989 |
| EP | 0 409 227 A2 | 1/1991 |
| EP | 0 382 526 | 5/1996 |
| WO | WO 95 07086 | 3/1995 |
| WO | 95/07287 | 3/1995 |
| WO | 95/32984 | 12/1995 |
| WO | 96/13512 | 5/1996 |
| WO | 96/40164 | 12/1996 |
| WO | WO 97/09052 | 3/1997 |
| WO | WO 98 16186 | 4/1998 |

OTHER PUBLICATIONS

Gosselin G et al., "Anti–HIV Activities of the beta–L Enantiomer of 2',3'–Dideoxycytidine and its 5–Fluoro Derivative in Vitro", Antimicrobial Agents and Chemotherapy, 38, Jun 6, 1994 pp. 1292–1297.
Tsai et al., in Biochem. Pharmacol. (1994), pp. 1477–1481. vol. 48(7).
Mahmoudian, Pharm. Research vol. 8, No. 1, pp. 43–46 (1991).
Lin, et al., in J. Med. Chem. vol. 31, No. 2, pp. 336–340 (1988).

*Primary Examiner*—Johann Richter
*Assistant Examiner*—L E Crane
(74) *Attorney, Agent, or Firm*—Sherry M. Knowles, Esq.; King & Spalding

(57) ABSTRACT

Compounds and pharmaceutical compositions active against hepatitis B virus are provided, as is a method for the treatment of hepatitis B virus infection in humans and other host animals is provided comprising administering an effective amount of a β-L-(2'or 3'-azido)-2',3'-dideoxy-5-fluorocytosine of the formula

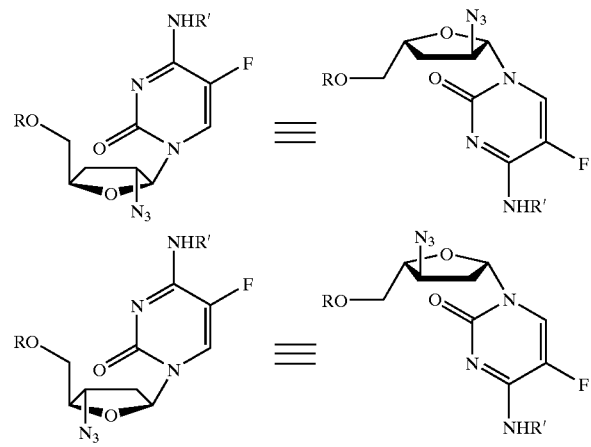

wherein R is H, acyl, monophosphate, diphosphate, or triphosphate, or a stabilized phosphate derivative (to form a stabilized nucleotide prodrug), and R' is H, acyl, or alkyl.

97 Claims, 6 Drawing Sheets

V = acyl [CH$_3$-C$_6$C$_5$H-C(=O)]
X = Leaving group [CH$_3$SO$_2$, CH$_3$C$_6$H$_4$SO$_2$, H, CF$_3$SO$_2$]
Y,Y' = F, N$_3$, NR$_1$R$_2$ [R$_1$,R$_2$ = H, alkyl, aryl],
    NO$_2$, NOR [R=H, alkyl, acyl], O-alkyl, O-aryl, etc.

NUCLEOSIDE WITH ANTI-HEPATITIS B VIRUS ACTIVITY

This application claims priority to U.S. Ser. No. 60/107,116, filed on Nov. 5, 1998, and U.S. Ser. No. 60/115,653, filed on Jan. 13, 1999 now abandoned.

This invention is in the area of methods for the treatment of hepatitis B virus (also referred to as "HBV") that includes administering an effective amount of one or more of a L-2' or 3'-azido)-2',3'-dideoxy-5-fluorocytosine to a host in need thereof.

BACKGROUND OF THE INVENTION

HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer. In western industrialized countries, high risk groups for HBV infection include those in contact with HBV carriers or their blood samples. The epidemiology of HBV is in fact very similar to that of acquired immunodeficiency syndrome, which accounts for why HBV infection is common among patients with AIDS or HIV-associated infections. However, HBV is more contagious than HIV.

Daily treatments with a-interferon, a genetically engineered protein, has shown promise. A human serum-derived vaccine has also been developed to immunize patients against HBV. Vaccines have been produced through genetic engineering. While the vaccine has been found effective, production of the vaccine is troublesome because the supply of human serum from chronic carriers is limited, and the purification procedure is long and expensive. Further, each batch of vaccine prepared from different serum must be tested in chimpanzees to ensure safety. In addition, the vaccine does not help the patients already infected with the virus.

A number of synthetic nucleosides have been identified which exhibit activity against HBV. The (−)-enantiomer of BCH-189 (2',3'-dideoxy-3'-thiacytidine), known as 3TC, claimed in U.S. Pat. No. 5,539,116 to Liotta, et al., is currently in clinical trials for the treatment of hepatitis B. See also EPA 0 494 119 A1 filed by BioChem Pharma, Inc.

β-2-Hydroxymethyl-5-(5-fluorocytosin-1-yl)-1,3-oxathiolane ("FTC"), claimed in U.S. Pat. Nos. 5,814,639 and 5,914,331 to Liotta, et al., exhibits activity against HBV. See Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" *Antimicrobial Agents and Chemotherapy,* December 1992, page 2686–2692; and Cheng, et al., *Journal of Biological Chemistry,* Volume 267(20), 13938–13942 (1992).

U.S. Pat. Nos. 5,565,438, 5,567,688 and 5,587,362 (Chu, et al.) disclose the use of 2'-fluoro-5-methyl-β-L-arabinofuranolyluridine (L-FMAU) for the treatment of hepatitis B and Epstein Barr virus.

Penciclovir (2-amino-1,9-dihydro-9-[4-hydroxy-3-(hydroxymethyl)butyl]-6H-purin-6-one; PCV) has established activity against hepatitis B. See U.S. Pat. Nos. 5,075,445 and 5,684,153.

Adefovir (9-[2-(phosphonomethoxy)ethyl]adenine, also referred to as PMEA or [[2-(6-amino-9H-purin-9-yl)ethoxy] methylphosphonic acid), also has established activity against hepatitis B. See for example U.S. Pat. Nos. 5,641,763 and 5,142,051.

Yale University and The University of Georgia Research Foundation, Inc. disclose the use of L-FDDC (5-fluoro-3'-thia-2',3'-dideoxycytidine) for the treatment of hepatitis B virus in WO 92/18517.

Other drugs explored for the treatment of HBV include adenosine arabinoside, thymosin, acyclovir, phosphonoformate, zidovudine, (+)-cyanidanol, quinacrine, and 2'-fluoroarabinosyl-5-iodouracil.

U.S. Pat. Nos. 5,444,063 and 5,684,010 to Emory University disclose the use of enantiomerically pure β-D-1,3-dioxolane purine nucleosides to treat hepatitis B.

WO 96/40164 filed by Emory University, UAB Research Foundation, and the Centre National de la Recherche Scientifique discloses a number of β-L-2',3'-dideoxynucleosides for the treatment of hepatitis B.

WO 95/07287 also filed by Emory University, UAB Research Foundation, and the Centre National de la Recherche Scientifique discloses 2' or 3' deoxy and 2',3'-dideoxy-β-L-pentofuranosyl nucleosides for the treatment of HIV infection.

WO96/13512 filed by Genencor International, Inc., and Lipitek, Inc., discloses the preparation of L-ribofuranosyl nucleosides as antitumor agents and virucides.

WO95/32984 discloses lipid esters of nucleoside monophosphates as immunosuppresive drugs.

DE4224737 discloses cytosine nucleosides and their pharmaceutical uses.

Tsai, et al., in Biochem. Pharmacol. 48(7), pages 1477–81, 1994 disclose the effect of the anti-HIV agent 2'-β-D-F-2',3'-dideoxynucleoside analogs on the cellular content of mitochondrial DNA and lactate production.

Galvez, J. Chem. Inf. Comput. Sci. (1994), 35(5), 1198–203 describes molecular computation of β-D-3β-azido-2',3'-dideoxy-5-fluorocytidine.

Mahmoudian, Pharm. Research 8(1), 43–6 (1991) discloses quantitative structure-activity relationship analyses of HIV agents such as β-D-3'-azido-2',3'-dideoxy-5-fluorocytidine.

U.S. Pat. No. 5,703,058 discloses (5-carboximido or 5-fluoro)-(2',3'-unsaturated or 3'-modified) pyrimidine nucleosides for the treatment of HIV or HBV.

Lin, et al., discloses the synthesis and antiviral activity of various 3'-azido analogues of β-D-nucleosides in J. Med. Chem. 31(2), 336–340 (1988).

An essential step in the mode of action of purine and pyrimidine nucleosides against viral diseases, and in particular, HBV and HIV, is their metabolic activation by cellular and viral kinases, to yield the mono-, di-, and triphosphate derivatives. The biologically active species of many nucleosides is the triphosphate form, which inhibits DNA polymerase or reverse transcriptase, or causes chain termination. The nucleoside derivatives that have been developed for the treatment of HBV and HIV to date have been presented for administration, to the host in unphosphorylated form, notwithstanding the fact that the nucleoside must be phosphorylated in the cell prior to exhibiting its antiviral effect, because the triphosphate form has typically either been dephosphorylated prior to reaching the cell or is poorly absorbed by the cell. Nucleotides in general cross cell membranes very inefficiently and are generally not very not very potent in vitro. Attempts at modifying nucleotides to increase the absorption and potency of nucleotides have been described by R. Jones and N. Bischofberger, *Antiviral Research*, 27 (1995) 1–17, the contents of which are incorporated herein by reference.

In light of the fact that hepatitis B virus has reached epidemic levels worldwide, and has severe and often tragic effects on the infected patient, there remains a strong need to provide new effective pharmaceutical agents to, treat humans infected with the virus that have low toxicity to the host.

Therefore, it is an object of the present invention to provide compounds, compositions and methods for the treatment of human patients or other hosts infected with HBV.

SUMMARY OF THE INVENTION

A method for the treatment of HBV infection in humans and other host animals is disclosed that includes administering an effective amount of a β-L-(2' or 3'-azido)-2',3'-dideoxy-5-fluorocytosine nucleoside or a pharmaceutically acceptable salt, ester, or prodrug thereof, including a stabilized phosphate, administered either alone or in combination or alternation with another anti-HBV agent, optionally in a pharmaceutically acceptable carrier; In a preferred embodiment, the 2' or 3'-azido group is in the ribosyl configuration. In a preferred embodiment, the nucleoside is provided as the indicated enantiomer and substantially in the absence of its corresponding β-D-enantiomer.

In one embodiment, the active compound is β-L-(2'-azido)-2',3'-dideoxy-5-fluorocytosine (L-2'-A-5-FddC) or a pharmaceutically acceptable ester, salt or prodrug thereof of the formula:

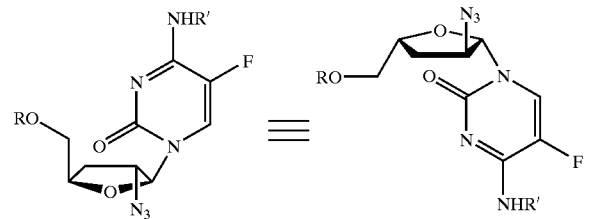

wherein R is H, acyl, monophosphate, diphosphate, or triphosphate, or a stabilized phosphate derivative (to form a stabilized nucleotide prodrug), and R' is hydrogen, acyl, or alkyl.

In another embodiment, the active compound is β-L-(3'-azido)-2',3'-dideoxy-5-fluorocytosine (L-3'-A-5-FddC) or a pharmaceutically acceptable ester, salt or prodrug thereof of the formula:

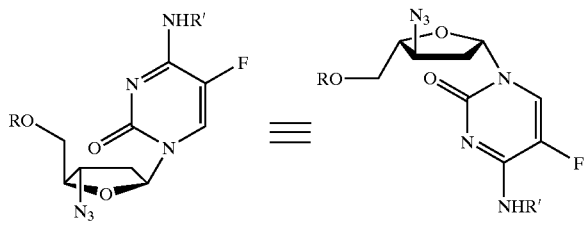

wherein R is H, acyl, monophosphate, diphosphate, or triphosphate, or a stabilized phosphate derivative (to form a stabilized nucleotide prodrug), and r' is hydrogen, acyl, or alkyl.

The disclosed nucleosides, or their pharmaceutically acceptable prodrugs, esters or salts or pharmaceutically acceptable formulations containing these compounds are useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In one embodiment, the invention includes a method for the treatment of humans infected with HBV that includes administering an HBV treatment amount of a prodrug of the specifically disclosed L-(2' or 3')-A-5-FddC nucleosides. A prodrug, as used herein, refers to a pharmaceutically acceptable derivative of the specifically disclosed nucleoside, that is converted into the nucleoside on administration in vivo, or that has activity in itself. Nonlimiting examples are the 5' and N⁴-cytosine acylated or alkylated derivatives of the active compound, as well as the 5'-monophosphate, diphosphate, or triphosphate derivatives, other phosphates, or stablized nucleotide prodrugs, as described in more detail below. For example, the nucleoside is provided as the monophosphate, diphosphate or triphosphate in a formulation that protects the compound from dephosphorylation. Formulations include liposomes, lipospheres, microspheres or nanospheres (of which the latter three can be targeted to infected cells).

In one embodiment of the invention, one or more of the active compounds is administered in alternation or combination with one or more other anti-HBV agents, to provide effective anti-HBV treatment. Examples of anti-HBV agents that can be used in alternation or combination therapy include but are not limited to the cis-2-hydroxymethyl-5-(5-fluorocytosin-1-yl)-1,3-oxathiolane, preferably substantially in the form of the (−)-optical isomer ("FTC", see WO 92/14743); the (−)-enantiomer of cis-2-hydroxymethyl-5-(cytosin-1-yl)-1,3-oxathiolane (3TC); β-D-1,3-dioxolane purine nucleosides as described in U.S. Pat. Nos. 5,444,063 and 5,684,010; carbovir, interferon penciclovir and famciclovir.

Any method of alternation can be used that provides treatment to the patient. Nonlimiting examples of alternation patterns include 1–6 weeks of administration of an effective amount of one agent followed by 1–6 weeks of administration of an effective amount of a second anti-HBV agent. The alternation schedule can include periods of no treatment. Combination therapy generally includes the simultaneous administration of an effective ratio of dosages of two or more anti-HBV agents.

In light of the fact that HBV is often found in patients who are also anti-HIV antibody or HIV-antigen positive or who have been exposed to HIV, the active anti-HBV compounds disclosed herein or their derivatives or prodrugs can be administered in the appropriate circumstance in combination or alternation with anti-HIV medications.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data collected in vitro and in vivo for a number of antiviral compounds is found in Schinazi, et al, Mutations in retroviral genes associated with drug resistance, *International Antiviral News,* Volume 1(4), International Medical Press 1996.

Preferred examples of antiviral agents that can be used in combination or alternation with the compounds disclosed herein for HBV therapy include 2-hydroxymethyl-5-(5-fluorocytosin-1-yl)-1,3-oxathiolane (FTC); the (−)-enantiomer of 2-hydroxymethyl-5-(cytosin-1-yl)-1,3-oxathiolane (3TC); carbovir, acyclovir, interferon, L-FMAU, and β-D-dioxolane nucleosides such as β-D-dioxolanyl-guanine (DXG), β-D-dioxolanyl-2,6-diaminopurine (DAPD), and β-D-dioxolanyl-6-chloropurine (ACP), L-FDDC (5-fluoro-3'-thia-2',3'-dideoxycytidine), L-enantiomers of 3'-fluoro-modified β-2'-deoxyribonucleoside 5'-triphosphates, famciclovir, penciclovir, bis-Pom PMEA (adefovir, dipivoxil); lobucavir, ganciclovir, and ribavarin.

The active anti-HBV agents can also be administered in combination with antibiotics, other antiviral compounds, antifungal agents, or other pharmaceutical agents administered for the treatment of secondary infections.

DETAILED DESCRIPTION OF THE INVENTION

Figure 1:
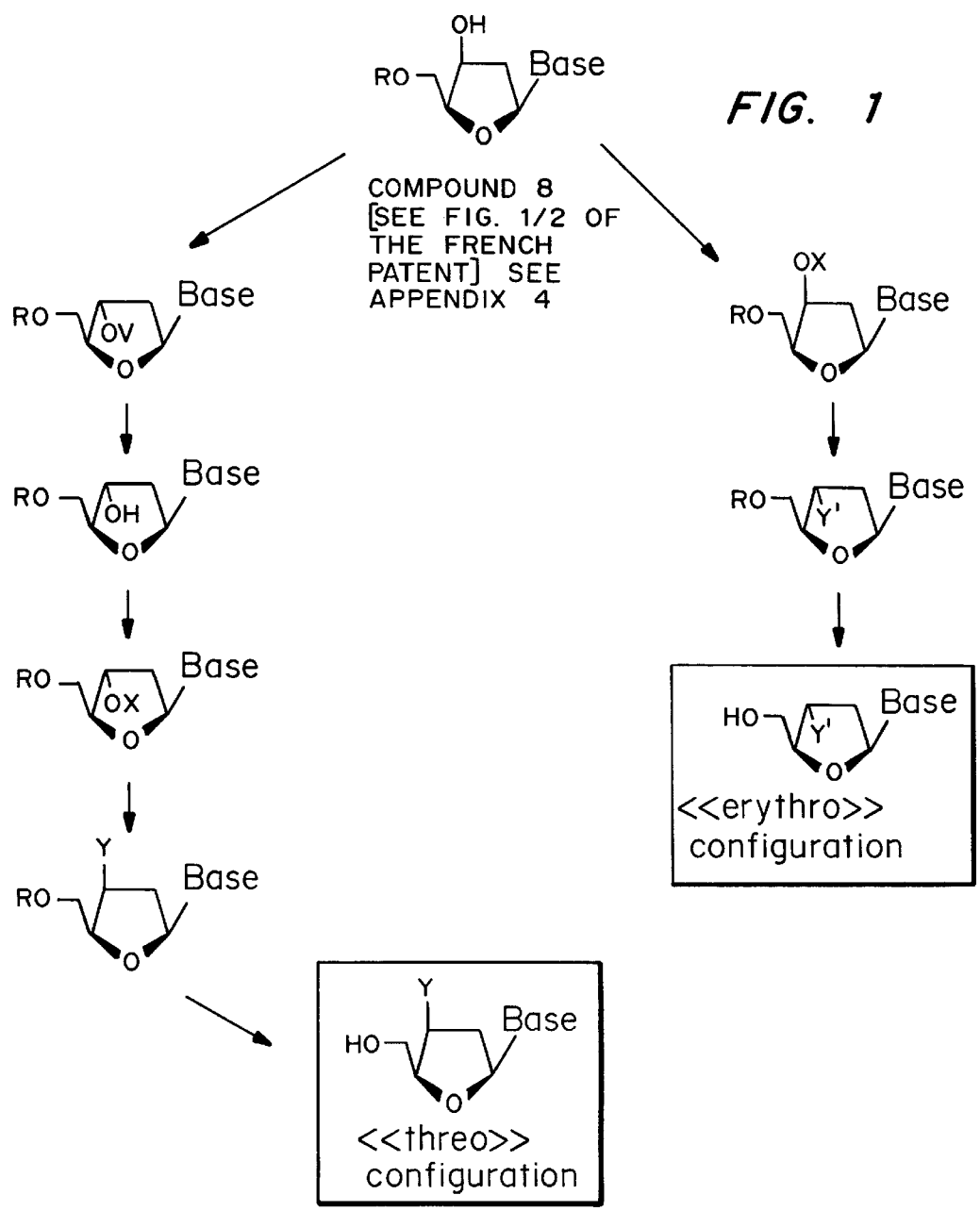
FIG. 1 is an illustration of a general reaction scheme for the stereospecific synthesis of 3'-substituted β-L-dideoxynucleosides.

As used herein, the term "substantially in the form of" or "substantially in the absence of" or "substantially free of" refers to a nucleoside composition that includes at least approximately 95%, and preferably approximately 97%, 98%, 99%, or 100% of a single enantiomer of that nucleoside.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, butyl, isobutyl, t-butyl, pentyl, cylcobutyl, cyclopropyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991. The term lower alkyl, as used herein, and unless otherwise specified, refers to a $C_1$ to $C_4$ ethyl, propyl, butyl, pentyl, hexyl, isopropyl, isobutyl, sec-butyl, or t-butyl group.

As used herein, the term acyl specifically includes but is not limited to C(O)alkyl, C(O)aryl, acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic, or a the residue of an amino acid moiety.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

As used herein, the term amino acid includes natural and unnatural amino acids and includes but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

A prodrug, as used herein, refers to a pharmaceutically acceptable derivative of the specifically disclosed nucleoside, that is converted into the nucleoside on administration in vivo, or that has activity in itself. Nonlimiting examples are the 5' and $N^4$-cytosine acylated or alkylated derivatives of the active compound, as well as the 5'-monophosphate, diphosphate, or triphosphate derivatives, other phosphates, or stablized nucleotide prodrugs, or 5'-ether lipids as described in more detail below. For example, the nucleoside is provided as the monophosphate, diphosphate or triphosphate in a formulation that protects the compound from dephosphorylation. Formulations include liposomes, lipospheres, microspheres or nanospheres (of which the latter three can be targeted to infected cells).

The invention as disclosed herein is a method and composition for the treatment of HBV infection and other viruses replicating in a like manner, in humans or other host animals, that includes administering an effective HBV-treatment amount of one or more of the above-identified compounds, or a physiologically acceptable derivative, or a physiologically acceptable salt thereof, optionally in a pharmaceutically acceptable carrier. The compounds of this invention either possess anti-HBV activity, or are metabolized to a compound or compounds that exhibit anti-HBV activity.

Structure and Preparation of Active Nucleosides
 Stereochemistry

Since the 1' and 4' carbons of the sugar (referred to below generically as the sugar moiety) of the nucleosides are chiral, their nonhydrogen substituents ($CH_2OR$ and the pyrimidine or purine base, respectively) can be either cis (on the same side) or trans (on opposite sides) with respect to the sugar ring system. The four optical isomers therefore are represented by the following configurations (when orienting the sugar moiety in a horizontal plane such that the "primary" oxygen (that between the C1' and C4'-atoms is in back): "β" or "cis" (with both groups "up", which corresponds to the configuration of naturally occurring nucleosides, i.e., the D configuration), "β" or cis (with both groups "down", which is a nonnaturally occurring configuration, i.e., the L configuration), "α" or "trans" (with the C2 substituent "up" and the C5 substituent "down"), and "α" or trans (with the C2 substituent "down" and the C5 substituent "up").

The active nucleosides of the present invention are in the β-L-configuration, with the azido group in the ribosyl configuration.

Prodrug Formulations

The nucleosides disclosed herein can be administered as any derivative that upon administration to the recipient, is capable of providing directly or indirectly, the parent active compound, or that exhibits activity in itself. In one embodiment, the hydrogen of the 5'-OH group is replaced by a $C_1$–$C_{20}$ alkyl; acyl including those in which the non-carbonyl moiety of the ester group is selected from straight, branched, or cyclic $C_1$–$C_{20}$ alkyl, phenyl, or benzyl; a naturally occurring or nonnaturally occurring amino acid; a 5'-ether lipid or a 5'-phosphoether lipid; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy; a dicarboxylic acid such as succinic acid; sulfonate esters such as alkyl or aralkyl sulphonyl including methanesulfonyl; or a mono, di or triphosphate ester.

One or both hydrogens of the amino groups on the purine or pyrimidine base can be replaced by a $C_1$–$C_{20}$ alkyl; acyl in which the non-carbonyl moiety of the ester group is selected from straight, branched, or cyclic $C_1$–$C_{20}$ alkyl, phenyl, or benzyl; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy.

The active nucleoside can also be provided as a 5'-ether lipid, as disclosed in the following references, which are incorporated by reference herein: Kucera, L. S., N. Iyer, E. Leake, A. Raben, Modest E. J., D. L. W., and C. Piantadosi. 1990. Novel membrane-interactive ether lipid analogs that inhibit infectious HIV-1 production and induce defective virus formation. AIDS Res Hum Retroviruses. 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. Synthesis and evaluation of novel ether lipid nucleoside conjugates for anti-HIV activity. J Med Chem. 34:1408.1414; Hostetler, K. Y., D. D. Richman, D. A. Carson, L. M. Stuhmiller, G. M. T. van Wijk, and H. van den Bosch. 1992. Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine. Antimicrob Agents Chemother. 36:2025.2029; Hostetler, K. Y., L. M. Stuhmiller, H. B. Lenting, H. van den Bosch, and D. D. Richman, 1990. Synthesis and antiretroviral activity of phospholipid analogs of azidothymidine and other antiviral nucleosides. J. Biol Chem. 265:6112.7.

Stablized Nucleotides

Any of the nucleosides described herein can be administered as a nucleotide prodrug or phospholipid prodrug to increase the activity, bioavailability, stability or otherwise alter the properties of the nucleoside. A number of nucleotide prodrug ligands are known. In general, alkylation, acylation or other lipophilic modification of the mono, di or triphosphoate of the nucleoside will increase the stability of the nucleotide. Examples of substituent groups that can replace one or more hydrogens on the the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect. Nonlimiting examples of nucleotide prodrugs are described in the following references.

Ho, D. H. W. (1973) Distribution of Kinase and deaminase of 1b-D-arabinofuranosylcytosine in tissues of man and muse. *Cancer Res.* 33, 2816–2820; Holy, A. (1993) Isopolar phosphorous-modified nucleotide analogues. In: De Clercq (Ed.), Advances in Antiviral Drug Design, Vol. I, JAI Press, pp. 179–231; Hong, C. I., Nechaev, A., and West, C. R. (1979a) Synthesis and antitumor activity of 1b-D-arabinofuranosylcytosine conjugates of cortisol and cortisone. *Biochem. Biophys. Rs. Commun.* 88, 1223–1229; Hong, C. I., Nechaev, A., Kirisits, A. J. Buchheit, D. J. and West, C. R. (1980) Nucleoside conjugates as potential antitumor agents. 3. Synthesis and antitumor activity of 1-(b-D-arabinofuranosyl)cytosine conjugates of corticosteriods and selected lipophilic alcohols. *J. Med. Chem.* 28, 171–177; Hostetler, K. Y., Stuhmiller, L. M., Lenting, H. B. M. van den Bosch, H. and Richman, D. D. (1990) Synthesis and antiretrioviral activity of phospholipid analogs of azidothymidine and other antiviral nucleosides. *J. Biol. Chem.* 265, 6112–6117; Hostetler, K. Y., Carson, D. A. and Richman, D. D. (1991); Phosphatidylazidothymidine: mechanism of antiretroviral action in CEM cells. *J Biol. Chem.* 266, 11714–11717; Hostetler, K. Y., Korba, B. Sridhar, C., Gardener, M. (1994a) Antiviral activity of phosphatidyl-dideoxycytidine in hepatitis B-infected cells and enhanced hepatic uptake in mice. *Antiviral Res.* 24, 59–67; Hostetler, K. Y., Richman, D. D., Sridhar, C. N. Felgner, P. L, Felgner, J., Ricci, J., Gardener, M. F. Selleseth, D. W. and Ellis, M. N. (1994b) Phosphatidylazidothymidine and phosphatidyl-ddC: Assessment of uptake in mouse lymphoid tissues and antiviral activities in human immunodeficiency virus-infected cells and in rauscher leukemia virus-infected mice. *Antimicrobial Agents Chemother.* 38, 2792–2797; Hunston, R. N., Jones, A. A. McGuigan, C., Walker, R. T., Balzarini, J., and De Clercq, E. (1984) Synthesis and biological properties of some cyclic phosphotriesters derived from 2'-deoxy-5-fluorouridine. J. Med. Chem. 27, 440–444; Ji, Y. H., Moog, C., Schmitt, G., Bischoff, P. and Luu, B. (1990); Monophosphoric acid, diesters of 7b-hydroxycholesterol and of pyrimidine nucleosides as potential antitumor agents: synthesis and preliminary evaluation of antitumor activity. *J. Med. Chem.* 33, 2264–2270; Jones, A. S., McGuigan, C., Walker, R. T., Balzarini, J. and DeClercq, E. (1984) Synthesis, properties, and biological activity of some nucleoside cyclic phosphoramidates. *J Chem. Soc. Perkin Trans.* I, 1471–1474; Juodka, B. A. and Smrt, J. (1974) Synthesis of ditribonucleoside phosph(P®N) amino acid derivatives. Coll. Czech. Chem. Comm. 39, 363–968; Kataoka, S., Imai, J., Yamaji, N., Kato, M., Saito, M., Kawada, T. and Imai, S. (1989) Alkylacted cAMP derivatives; selective synthesis and biological activities. *Nucleic Acids Res. Sym. Ser.,* 21, 1–2; Kataoka, S., Uchida, R. and Yamaji, N. (1991) A convenient synthesis of adenosine 3',5' cyclic phosphate (cAMP) benzyl and methyl triesters. *Heterocycles* 32, 1351–1356; Kinchington, D., Harvey, J. J., O'Connor, T. J., Jones, B. C. N. M., Devine, K. G., Taylor-Robinson, D., Jeffries, D. J. and McGuigan, C. (1992) Comparison of antiviral effects of zidovudine phosphoramidate and phosphorodiamidate derivatives against HIV and ULV in vitro. Antiviral Chem. Chemother. 3, 107–112; Kodama, K., Morozumi, M., Saitoh, K. I., Kuninaka, H., Yoshino, H. and Saneyoshi, M. (1989) Antitumor activity and pharmacology of 1-b-D-arabinofuranosylcytosine-5'-stearylphosphate; an orally active derivative of 1-b-D-arabinofuranosylcytosine. Jpn. J. Cancer Res. 80, 679–685; Korty, M. and Engels, J. (1979) The effects of adenosine- and guanosine 3',5'phosphoric and acid benzyl esters on guinea-pig ventricular myocardium. Naunyn-Schmiedeberg's Arch. Pharmacol. 310, 103–111; Kumar, A., Goe, P. L., Jones, A. S. Walker, R. T. Balzarini, J. and De Clercq, E. (1990) Synthesis and biological evaluation of some cyclic phosphoramidate nucleoside derivatives. *J. Med Chem.* 33, 2368–2375; LeBec, C., and Huynh-Dinh, T. (1991) Synthesis of lipophilic phosphate triester derivatives of 5-fluorouridine and arabinocytidine as anticancer prodrugs. *Tetrahedron Lett.* 32,6553–6556; Lichtenstein, J., Barner, H. D. and Cohen, S. S. (1960) The metabolism of exogenously supplied nucleotides by *Escherichia coli., J. Biol. Chem.* 235, 457–465; Lucthy, J., Von Daeniken, A., Friederich, J. Manthey, B., Zweifel, J., Schlatter, C. and Benn, M. H. (1981) Synthesis and toxicological properties of three naturally occurring cyanoepithioalkanes. Mitt. Geg. Lebensmittelunters. *Hyg.* 72, 131–133 (*Chem. Abstr.* 95, 127093); McGuigan, C. Tollerfield, S. M. and Riley, P. A. (1989) Synthesis and biological evaluation of some phosphate triester derivatives of the anti viral drug Ara. *Nucleic Acids Res.* 17, 6065–6075; McGuigan, C., Devine, K. G., O'Connor, T. J., Galpin, S. A., Jeffries, D. J. and Kinchington, D. (1990a) Synthesis and evaluation of some novel phosphoramidate derivatives of 3'-azido-3'-deoxythymidine (AZT) as anti-HIV compounds. *Antiviral Chem. Chemother.* 1, 107–113; McGuigan, C., O'Connor, T. J., Nicholls, S. R. Nickson, C. and Kinchington, D. (1990b) Synthesis and anti-HIV activity of some novel substituted dialky phosphate derivatives of AZT and ddCyd. *Antiviral Chem. Chemother.* 1, 355–360; McGuigan, C., Nicholls, S. R., O'Connor, T. J., and Kinchington, D. (1990c) Synthesis of some novel dialkyl phosphate derivative of 3'-modified nucleosides as potential anti-AIDS drugs. *Antiviral Chem. Chemother.* 1, 25–33; McGuigan, C., Devine, K. G.; O'Connor, T. J., and Kinchington, D.(1991) Synthesis and anti-HIV activity of some haloalky phosphoramidate derivatives of 3'-azido-3'deoxythylmidine (AZT); potent activity of the trichloroethyl methoxyalaninyl compound. *Antiviral Res.* 15, 255–263; McGuigan, C., Pathirana, R. N., Mahmood, N., Devine, K. G. and Hay, A. J. (1992) Aryl phosphate derivatives of AZT retain activity against HIV1 in cell lines which are resistant to the action of AZT. *Antiviral Res.* 17, 311–321; McGuigan, C., Pathirana, R. N., Choi, S. M., Kinchington, D. and O'Connor, T. J. (1993a) Phosphoramidate derivatives of AZT as inhibitors of HIV; studies on the carboxyl terminus. *Antiviral Chem. Chemother.* 4, 97–101; McGuigan, C., Pathirana, R. N., Balzarini, J. and De Clercq, E. (1993b) Intracellular delivery of bioactive AZT nucleotides by aryl phosphate derivatives of AZT. *J. Med. Chem.* 36, 1048–1052.

Alkyl hydrogen phosphonate derivatives of the anti-HIV agent AZT may be less toxic than the parent nucleoside analogue. *Antiviral Chem. Chemother.* 5, 271–277; Meyer, R. B., Jr., Shuman, D. A. and Robins, R. K. (1973) Synthesis of purine nucleoside 3',5'-cyclic phosphoramidates. *Tetrahedron Lett.* 269–272; Nagyvary, J. Gohil, R. N., Kirchner, C. R. and Stevens, J. D. (1973) Studies on neutral esters of cyclic AMP, *Biochem. Biophys. Res. Commun.* 55, 1072–1077; Namane, A. Gouyette, C., Fillion, M. P., Fillion, G. and Huynh-Dinh, T. (1992) Improved brain delivery of AZT using a glycosyl phosphotriester prodrug. J. Med. Chem. 35, 3039–3044; Nargeot, J. Nerbonne, J. M. Engels, J. and Leser, H. A. (1983) Natl. Acad. Sci. U.S.A. 80, 2395–2399; Nelson, K. A., Bentrude, W. G., Stser, W. N. and Hutchinson, J. P. (1987) The question of chair-twist equilibria for the phosphate rings of nucleoside cyclic 3',5'monophosphates. $^1$HNMR and x-ray crystallographic study of the diasteromers of thymidine phenyl cyclic 3',5'-monophosphate. J. Am. Chem. Soc. 109, 4058–4064; Nerbonne, J. M., Richard, S., Nargeot, J. and Lester, H. A. (1984) New photoactivatable cyclic nucleotides produce intracellular jumps in cyclic AMP and cyclic GMP concentrations. Nature 301, 74–76; Neumann, J. M., Hervé, M., Debouzy, J. C., Guerra, F. I., Gouyette, C., Dupraz, B. and Huynh-Dinh, T. (1989) Synthesis and transmembrane transport studies by NMR of a glucosyl phospholipid of thymidine. J. Am. Chem. Soc. 111, 4270–4277; Ohno, R., Tatsumi, N., Hirano, M., Imai, K. Mizoguchi, H., Nakamura, T., Kosaka, M., Takatuski, K., Yamaya, T., Toyama, K., Yoshida, T., Masaoka, T., Hashimoto, S., Ohshima, T., Kimura, I., Yamada, K. and Kimura, J. (1991) Treatment of myelodysplastic syndromes with orally administered 1-b-D-rabinofuranosylcytosine-5'stearylphosphate. Oncology 48, 451–455. Palomino, E., Kessle, D. and Horwitz, J. P. (1989) A dihydropyridine carrier system for sustained delivery of 2',3'dideoxynucleosides to the brain. J. Med. Chem. 32, 622–625; Perkins, R. M., Barney, S., Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) Activity of BRL47923 and its oral prodrug, SB203657A against a rauscher murine leukemia virus infection in mice. Antiviral Res. 20 (Suppl. I). 84; Piantadosi, C., Marasco, C. J., Jr., Morris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) Synthesis and evaluation of novel ether lipid nucleoside conjugates for anti-HIV-1 activity. J. Med. Chem. 34, 1408–1414; Pompon, A., Lefebvre, I., Imbach, J. L., Kahn, S. and Farquhar, D. (1994) Decomposition pathways of the mono- and bis (pivaloyloxymethyl) esters of azidothymidine-5'-monophosphate in cell extract and in tissue culture medium; an application of the 'on-line ISRP-cleaning' HPLC technique. Antiviral Chem. Chemother. 5, 91–98; Postemark, T. (1974) Cyclic AMP and cyclic GMP. Annu. Rev. Pharmacol. 14, 23–33; Prisbe, E. J., Martin, J. C. M., McGee, D. P. C., Barker, M. F. Smee, D. F. Duke, A. E., Matthews, T. R. and Verheyden, J. P. J. (1986) Synthesis and antiherpes virus activity of phosphate an phosphonate derivatives of 9-[(1, 3-dihydroxy-2-propoxy)methyl]guanine. J. Med. Chem. 29, 671–675; Pucch, F., Gosselin, G., Lefebvre, I., Pompon, A., Aubertin, A. M. Dim, A. and Imbach, J. L. (1993) Intracellular delivery of nucleoside monophosphate through a reductase-mediated activation process. Antiviral Res. 22, 155–174; Pugaeva, V. P., Klochkeva, S. I., Mashbits, F. D. and Eizengart, R. S. (1969). Toxicological assessment and health standard ratings for ethylene sulfide in the industrial atmosphere. Gig. Trf. Prof. Zabol. 13, 47–48 (Chem. Abstr. 72, 212); Robins, R. K. (1984) The potential of nucleotide analogs as inhibitors of retroviruses and tumors. Pharm. Res. 11–18; Rosowsky, A., Kim. S. H., Ross and J. Wick, M. M. (1982) Lipophilic 5'-(alkylphosphate) esters of 1-b-D- arabinofuranosylcytosine and its $N^4$-acyl and 2,2'-anhydro-3'O-acyl derivatives as potential prodrugs. J. Med. Chem. 25, 171–178; Ross, W. (1961) Increased sensitivity of the walker turnout towards aromatic nitrogen mustards carrying basic side chains following glucose pretreatment. Biochem. Pharm. 8, 235–240; Ryu, e. K., Ross, R. J. Matsushita, T., MacCoss, M., Hong, C. I. and West, C. R. (1982). Phospholipid-nucleoside conjugates. 3. Synthesis and preliminary biological evaluation of 1-b-D-arabinofuranosylcytosine 5'diphosphate[–], 2-diacylglycerols. J. Med. Chem. 25, 1322–1329; Saffhill, R. and Hume, W. J. (1986) The degradation of 5-iododeoxyurindine and 5-bromoeoxyuridine by serum from different sources and its consequences for the use of these compounds for incorporation into DNA. Chem. Biol. Interact. 57, 347–355; Saneyoshi, M., Morozumi, M., Kodama, K., Machida, J., Kuninaka, A. and Yoshino, H. (1980) Synthetic nucleosides and nucleotides. XVI. Synthesis and biological evaluations of a series of 1-b-D-arabinofuranosylcytosine 5'-alky or arylphosphates. Chem. Pharm. Bull. 28, 2915–2923; Sastry, J. K., Nehete, P. N., Khan, S., Nowak, B. J., Plunkett, W., Arlinghaus, R. B. and Farquhar, D. (1992) Membrane-permeable dideoxyuridine 5'-monophosphate analogue inhibits human immunodeficiency virus infection. Mol. Pharmacol. 41, 441–445; Shaw, J. P., Jones, R. J. Arimilli, M. N., Louie, M. S., Lee, W. A. and Cundy, K. C. (1994) Oral bioavailability of PMEA from PMEA prodrugs in male Sprague-Dawley rats. 9th Annual AAPS Meeting. San Diego, Calif. (Abstract). Shuto, S., Ueda, S., Imamura, S., Fukukawa, K. Matsuda, A. and Ueda, T. (1987) A facile one-step synthesis of 5'phosphatidyl-nucleosides by an enzymatic two-phase reaction. Tetrahedron Lett. 28, 199–202; Shuto, S., Itoh, H., Ueda, S., Imamura, S., Kukukawa, K., Tsujino, M., Matsuda, A. and Ueda, T. (1988) A facile enzymatic synthesis of 5'-(3-sn-phosphatidyl)nucleosides and their antileukemic activities. Chem. Pharm. Bull. 36, 209–217. A preferred phosphate prodrug group is the S-acyl-2-thioethyl group, also referred to as "SATE".

Preparation of the Active Compounds

Figure 2:
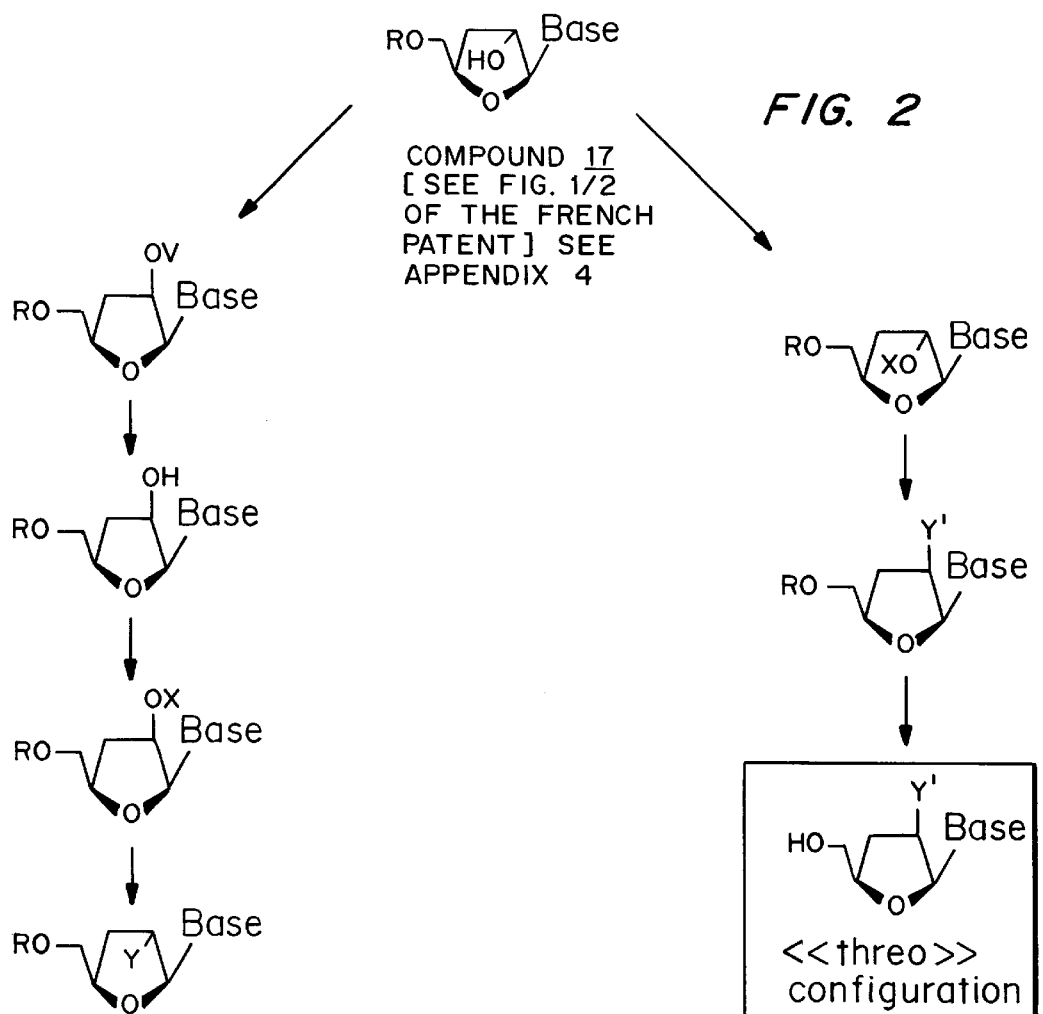
FIG. 2 is an illustration of a general reaction scheme for the stereospecific synthesis of 2'-substituted β-L-dideoxynucleosides.
Figure 3A:
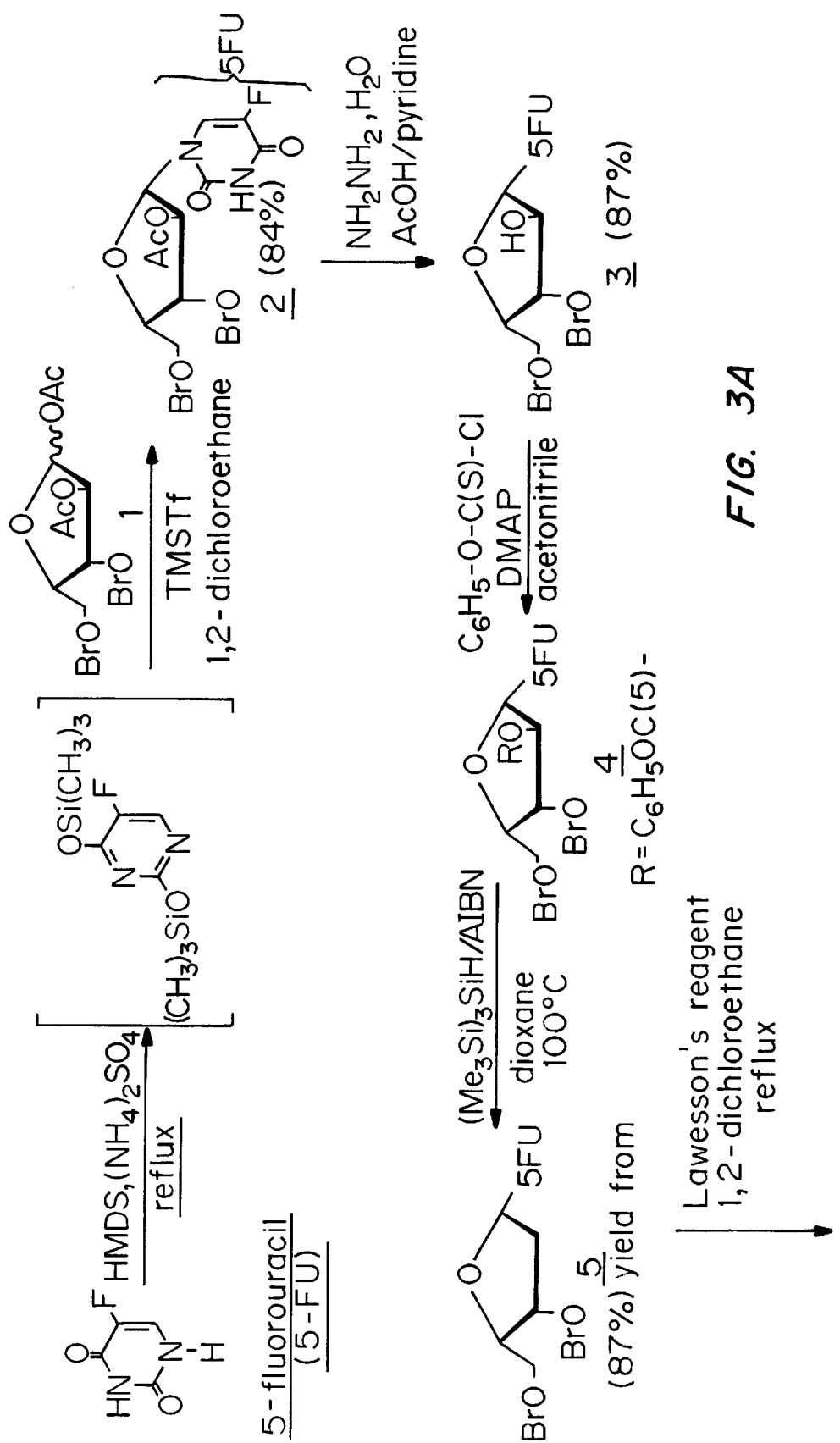
FIG. 3 is an illustration of one process for the preparation of β-L-(3'-azido)-2',3'-dideoxy-5-fluorocytosine (L-3'-A-5-FddC).
Figure 3B:
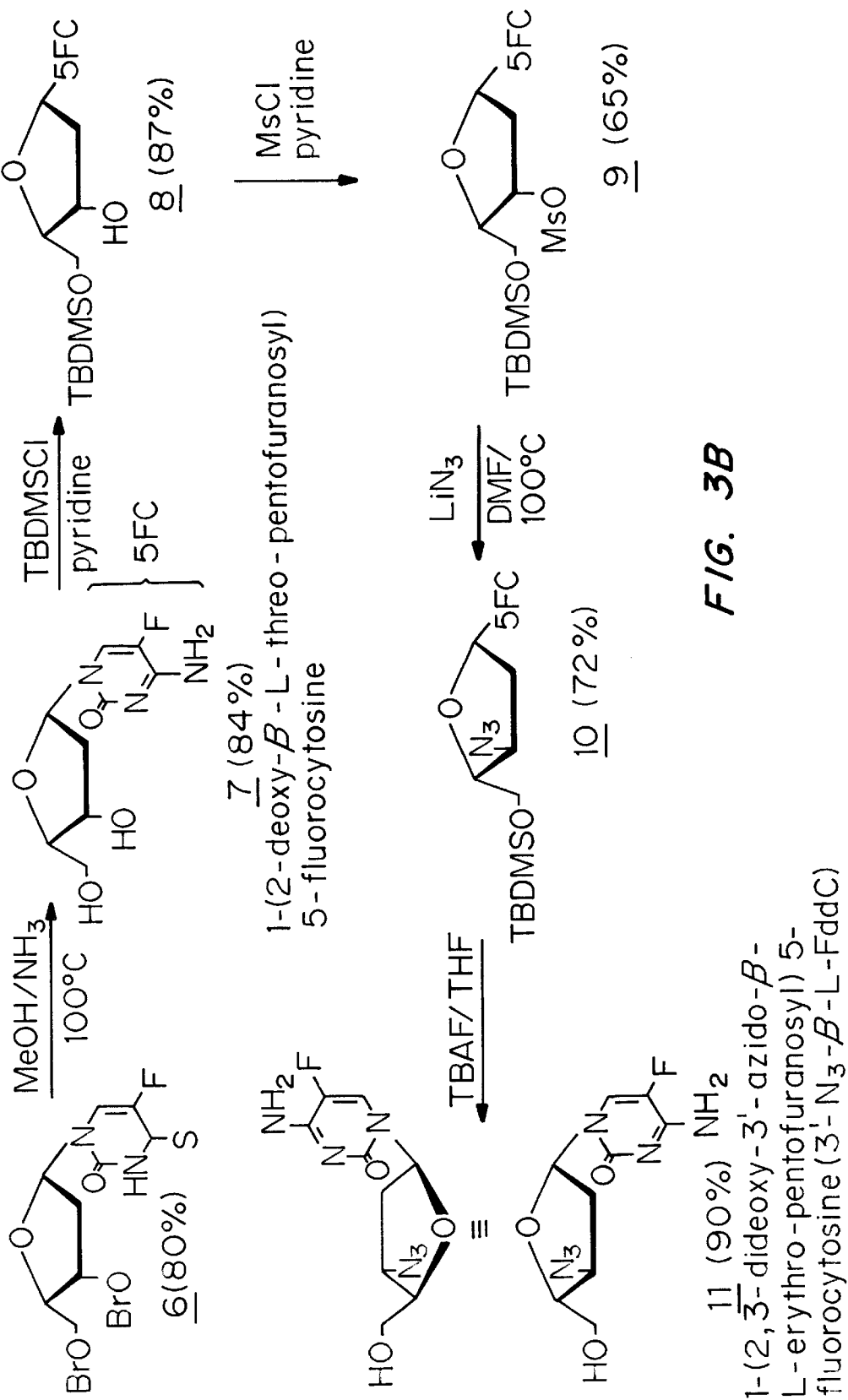
Figure 4A:
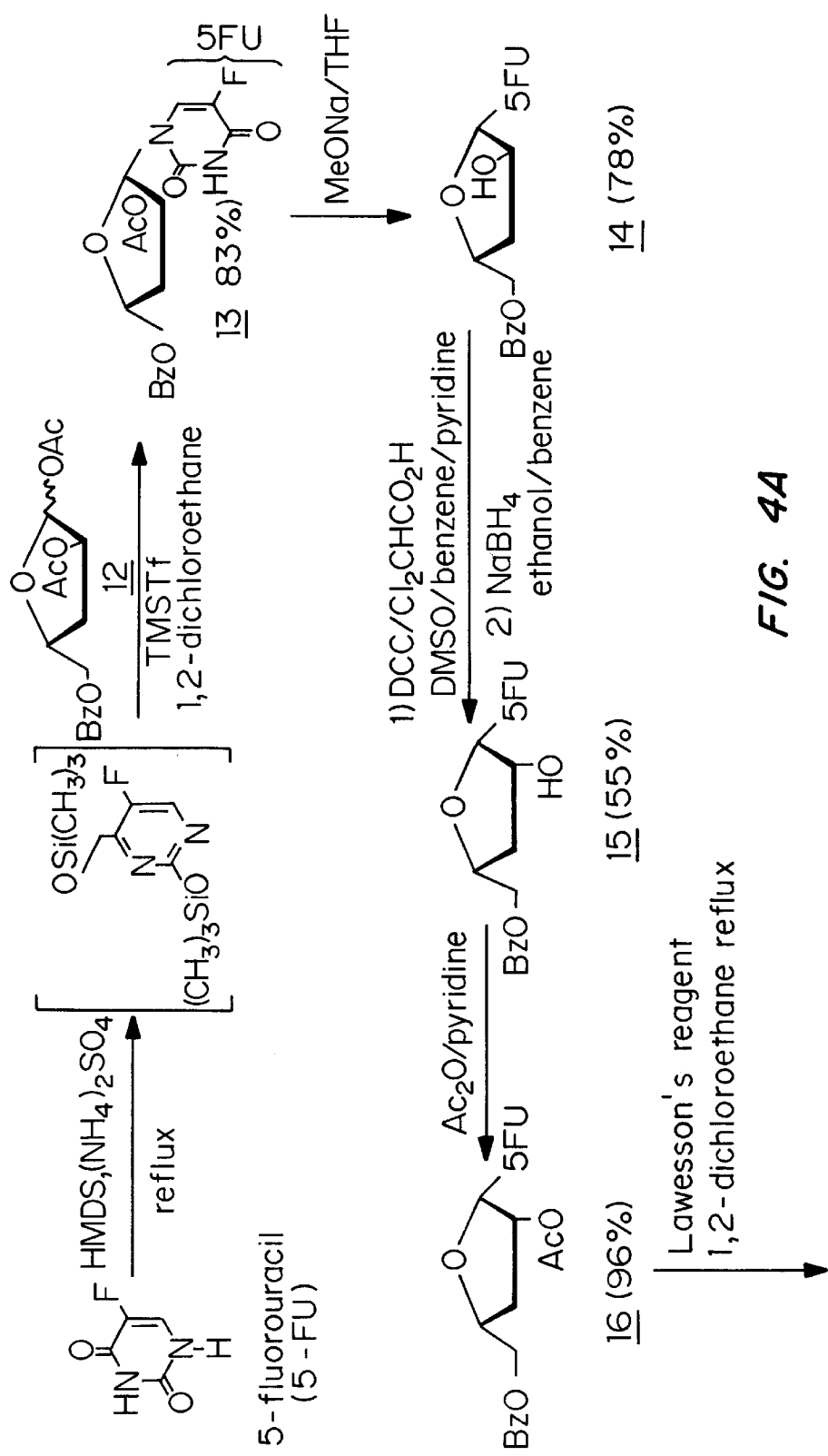
FIG. 4 is an illustration of one process for the preparation of β-L-(2'-azido)-2',3'-dideoxy-5-fluorocytosine (L-2'-A-5-FddC).
Figure 4B:
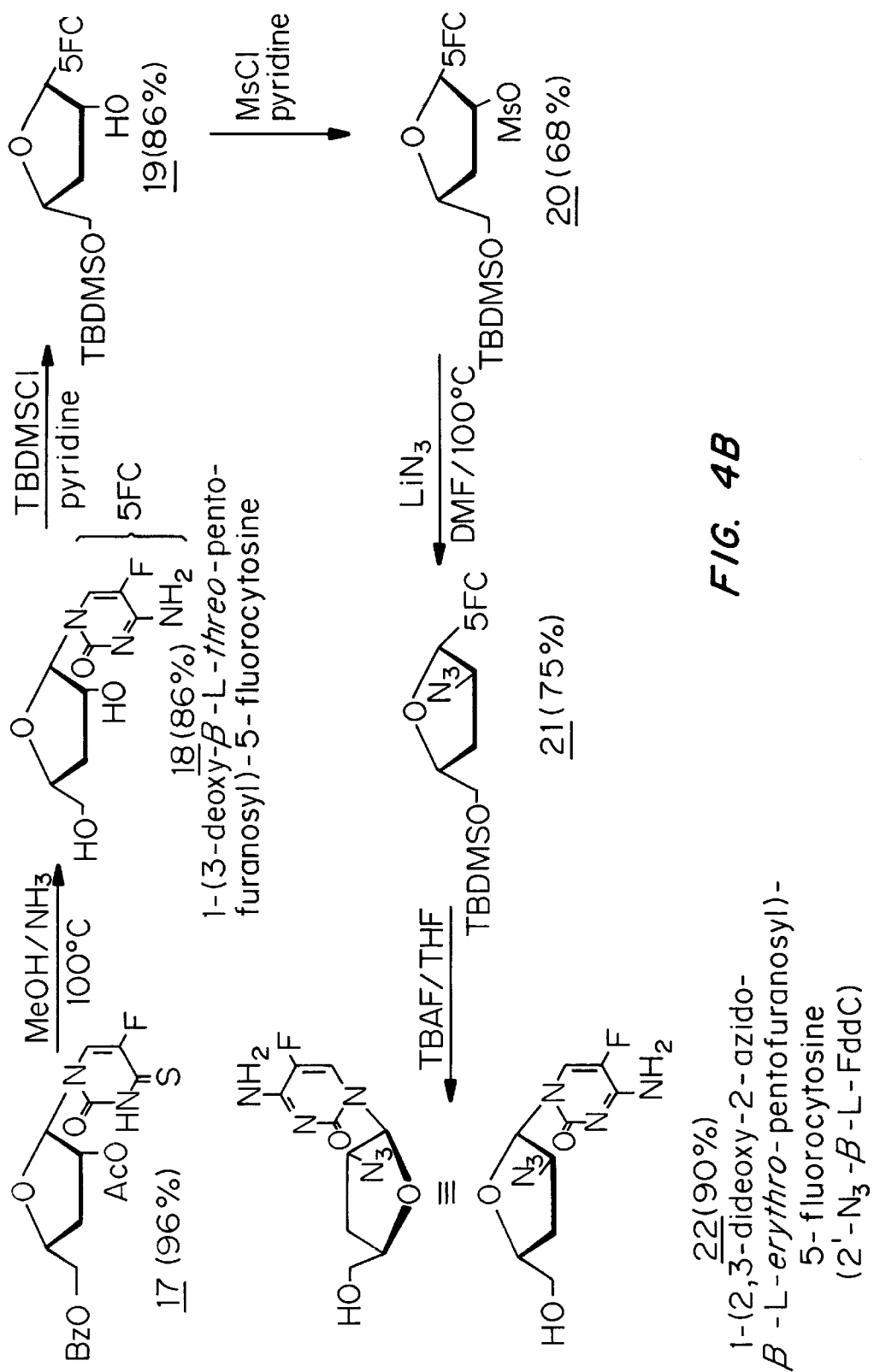

The nucleosides used in the disclosed method to treat HBV infections in a host organism can be prepared according to known methods. A general process for the stereospecific synthesis of 3'-substituted β-L-dideoxynucleosides is shown in FIG. 1. A general process for the steroespecific synthesis of 2'-substituted β-L-dideoxynucleosides is shown in FIG. 2. A detailed synthesis of β-L-(3'-azido)-2',3'-dideoxy-5-fluorocytosine is provided in FIG. 3. A detailed synthesis of β-L-(2'-azido)-2',3'-dideoxy)-5-fluorocytosine is provide in FIG. 4 and in Example 2 below.

EXAMPLE 1

Preparation of β-L-(3'-azido)-2',3'-dideoxy-5-fluorocytidine

Melting points were determined in open capillary tubes on a Gallenkamp MFB-595-010 M apparatus and are uncorrected. The UV absorption spectra were recorded on an Uvikon 931 (KONTRON) spectrophotometer in ethanol. $^1$H-NMR spectra were run at room temperature in DMSO-$d_6$ with a Bruker AC 250 or 400 spectrometer. Chemical shifts are given in ppm, DMSO-$d_5$ being set at 2.49 ppm as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive-(FAB>0) or negative (FAB<0) ion mode on a JEOL DX 300 mass spectrometer. The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg cm$^2$ g$^{-1}$. Elemental analysis were carried out by the "Service de Microanalyses du CNRS, Division de Vernaison" (France). Analyses indicated by the symbols of the elements or functions were within ±0.4% of theoretical values. Thin layer chromatography was performed on pre-coated aluminium sheets of Silica Gel 60 $F_{254}$ (Merck, Art. 5554), visualisation of products being accomplished by UV absorbency followed by charring with 10% ethanolic sulfuric acid and heating. Column chromatography was carried out on Silica Gel 60 (Merck, Art. 9385) at atmospheric pressure.

1-(2-O-Acetyl-3,5-di-O-Benzoyl-β-L-Xylofuranosyl)-5-Fluorouracil (2)

A suspension of 5-fluorouracil (5.0 g, 38.4 mmol) was treated with hexamethyldisilazane (HMDS, 260 mL) and a catalytic amount of ammonium sulfate during 18 h under reflux. After cooling to room temperature, the mixture was evaporated under reduced pressure, and the residue obtained as a colourless oil was diluted with anhydrous 1,2-dichloroethane (260 mL). To the resulting solution was added 1,2-di-O-acetyl-3,5-di-o-benzoyl-L-xylofuiranose 1 (11.3 g, 25.6 mmol) [Ref.: Gosselin, G.; Bergogne, M.-C.; Imbach, J.-L., "Synthesis and Antiviral Evaluation of β-L-Xylofuranosyl Nucleosides of the Five Naturally Occuring Nucleic Acid Bases", *Journal of Heterocyclic Chemistry*, 1993, 30 (October–November), 1229–1233] in anhydrous 1,2-dichloroethane (130 mL), followed by addition of trimethylsilyl trifluoromethanesulfonate (TMSTf, 9.3 mL, 51.15 mmol). The solution was stirred for 6 h at room temperature under argon atmosphere, then diluted with chloroform (1 L), washed with the same volume of a saturated aqueous sodium hydrogen carbonate solution and finally with water (2×800 mL). The organic phase was dried over sodium sulphate, then evaporated under reduced pressure. The resulting crude material was purified by silica gel column chromatography [eluent: stepwise gradient of methanol (0–4%) in methylene chloride] to give 2 (11.0 g, 84% yield) as a white foam; mp=96–98° C.; UV (ethanol): $\lambda_{max}$=228 nm ($\epsilon$=25900) 266 nm ($\epsilon$=9000), $\lambda_{min}$=250 nm ($\epsilon$=7200); $^1$H-NMR (DMSO-$d_6$): δ11.1 (br s, 1H, NH), 8.05 (1H, H-6, $J_{6-F5}$=6.8 Hz), 7.9–7.4 (m, 10H, 2 $C_6H_5$CO), 5.99 (d, 1H, H-1', $J_{1'-2'}$=3.1 Hz), 5.74 (dd, 1H, H-3', $J_{3'-2'}$=4.2 Hz and $J_{3'-4'}$=2.3 Hz), 5.54 (t, 1H, H-2', $J_{2'-1'}$=$J_{2'-3'}$=2.9 Hz), 4.8–4.6 (m, 3H, H-4', H-5' and H-5"); MS: FAB>0 (matrix GT) m/z 513 (M+H)$^+$, 383 (S)$^+$, 105 ($C_6H_5$CO)$^+$; FAB<0 (matrix GT) m/z 511 (M–H)$^-$, 469 (M–CH$_3$CO)$^-$, 129 (B)$^-$, 121 ($C_6H_5$CO$_2$)$^-$; $[\alpha]_D^{20}$=−91 (c, 0.88 DMSO); Anal $C_{25}H_{21}FN_2O_9$ (C, H, N, F).

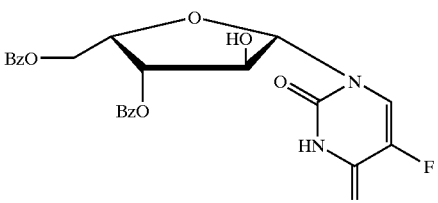

1-(3,5-Di-O-benzoyl-β-L-xylofuranosyl)-5-fluorouracil

Hydrazine hydrate (2.80 mL, 57.4 mmol) was added to a solution of 1-(2-O-acetyl-3,5-di-o-benzoyl-β-L-xylofuiranosyl)-5-fluorouracil 2 (9.80 g, 19.1 mmol) in acetic acid (35 mL) and pyridine (150 mL). The resulting solution was stirred overnight at room temperature. Acetone (50 mL) was added and the mixture was stirred during 2 h. The reaction mixture was concentrated to a small volume and partitioned between ethyl acetate (200 mL) and water (200 mL). Layers were separated and the organic phase was washed with a saturated aqueous sodium hydrogen carbonate solution (2×200 mL), and finally with water (2×200 mL). The organic phase was dried over sodium sulphate, then evaporated under reduced pressure. The resulting residue was purified by silica gel column chromatography [eluent: stepwise gradient of methanol (0–5%) in methylene chloride] to give pure 3 (7.82 g, 87%), which was crystallized from methylene chloride; mp=93–97° C.; UV (ethanol): $\lambda_{max}$=227 nm (ε=22800) 267 nm (ε=8200), $\lambda_{min}$=249 nm (ε=5900); $^1$H-NMR (DMSO-$d_6$): δ11.9 (br s, 1H, NH), 8.06 (d, 1H, H-6, $J_{6-F5}$=6.9 Hz), 8.0–7.4 (m, 10H, 2 $C_6H_5CO$), 6.35 (d, 1H, OH-2', $J_{OH-2'}$=3.8 Hz), 5.77 (d, 1H, H-1', $J_{1'-2'}$=3.3 Hz), 5.43 (dd, 1H, H-3', $J_{3'-2'}$=3.1 Hz and $J_{3'-4'}$=1.9 Hz) 4.8–4.6 (m, 3H, H-4', H-5' and H-5"), 4.43 (t, 1H, H-2', J=2.3 Hz); MS: FAB>0 (matrix GT) m/z 941 $(2M+H)^+$, 471 $(M+H)^+$, 341 $(S)^+$, 131 $(BH_2)^+$, 105 $(C_6H_5CO)^+$; FAB<0 (matrix GT) m/z 939 $(2M-H)^-$, 469 $(M-H)^-$, 129 $(B)^-$, 121 $(C_6H_5CO_2)^-$; $[\alpha]_D^{20}$=−110 (c, 1.55 DMSO).

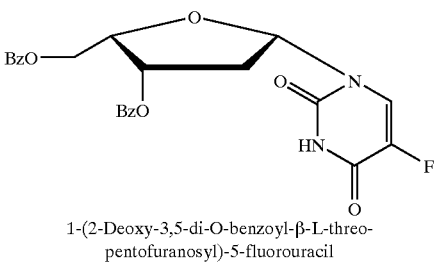

1-(2-Deoxy-3,5-di-O-benzoyl-β-L-threo-pentofuranosyl)-5-fluorouracil

To a solution of 1-(3,5-di-O-benzoyl-β-L-xylofuranosyl)-5-fluorouracil 3 (15.4 g, 32.7 mmol) in anhydrous acetonitrile (650 mL) were added O-phenyl chlorothionoformate (6.80 mL, 49.1 mmol) and 4-dimethylaminopyridine (DMAP, 12.0 g, 98.2 mmol). The resulting solution was stirred at room temperature under argon during 1 h and then evaporated under reduced pressure. The residue was dissolved in methylene chloride (350 mL) and the organic solution was successively washed with water (2×250 mL), with an ice-cold 0.5 N hydrochloric acid (250 mL) and with water (2×250 mL), dried over sodium sulphate and evaporated under reduced pressure. The crude material 4 was co-evaporated several times with anhydrous dioxane and dissolved in this solvent (265 mL). To the resulting solution were added under argon tris(trimethylsilyl)silane hydride (12.1 mL, 39.3 mmol) and α,α'-azoisobutyronitrile (AIBN, 1.74 g, 10.8 mmol). The reaction mixture was heated and stirred at 100° C. for 2.5 h under argon, then cooled to room temperature and evaporated under reduced pressure. The residue was purified by silica gel column chromatography [eluent: stepwise gradient of methanol (0–2%) in chloroform] to give pure 5 (13.0 g, 87%), which was crystallized from a diethyl ether/methanol mixture; mp=182–184° C.; UV (ethanol): $\lambda_{max}$=229 nm (ε=25800), 269 nm (ε=9300), $\lambda_{min}$=251 nm (ε=6500); $^1$H-NMR (DMSO-$d_6$): δ11.8 (br s, 1H, NH), 8.05 (d, 1H, H-6, $J_{6-F5}$=7.0 Hz), 8.0–7.4 (m, 10H, 2 $C_6H_5CO$), 6.15 (d, 1H, H-1', $J_{1'-2'}$=7.4 Hz), 5.68 (t, 1H, H-3', $J_{3'-2}$32 $J_{3'-4'}$=4.2 Hz), 4.8–4.6 (m, 2H, H-5' and H"-5), 4.6 (m, 1H, H-4'), 3.0–2.8 (m, 1H, H-2'), 2.5–2.3 (d, 1H, H-2", J=14.8 Hz); MS: FAB>0 (matrix GT) m/z 455 $(M+H)^+$, 325 $(S)^+$, 131 $(BH_2)^+$, 105 $(C_6H_5CO)^+$; FAB<0 (matrix GT) m/z 452 $(M-H)^-$, 129 $(B)^-$; $[\alpha]_D^{20}$=−125 (c 1.05 DMSO); Anal $C_{23}H_{19}FN_2O_7$ (C, H, N, F).

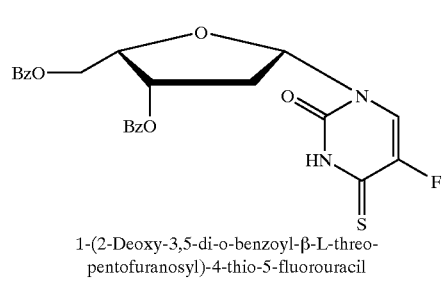

1-(2-Deoxy-3,5-di-o-benzoyl-β-L-threo-pentofuranosyl)-4-thio-5-fluorouracil

Lawesson's reagent (3.1 g, 7.70 mmol) was added under argon to a solution of 5.(5.0 g, 11.0 mmol) in anhydrous 1,2-dichloroethane (200 mL) and the reaction mixture was stirred overnight under reflux. The solvent was then evaporated under reduced pressure and the residue was purified by silica gel column chromatography [eluent: stepwise gradient of methanol (0–2%) in chloroform] to give the 4-thio intermediate 6 (80% yield) as a yellow foam; mp=178–179° C.; UV (ethanol): $\lambda_{max}$=230 nm (ε=24900), 273 nm (ε=6900), 333 nm (ε=19200), $\lambda_{min}$=258 nm (ε=5900), 289 nm (ε=5300); $^1$H-NMR (DMSO-$d_6$): δ13.1 (br s, 1H, NH), 8.10 (d, 1H, H-6, $J_{6-F5}$=4.6 Hz), 8.1–7.4 (m, 10H, 2 $C_6H_5CO$), 6.09 (d, 1H, H-1', $J_{1'-2'}$=7.3 Hz), 5.68 (t, 1H, H-3', $J_{3'-2'}$=$J_{3'-4'}$=4.1 Hz), 4.9–4.8 (m, 2H, H-5' and H-5"), 4.7 (m, 1H, H-4'), 2.9 (m, 1H, H-2'), 2.5 (m, 1H, H-2"); MS: FAB>0 (matrix GT) m/z 941 $(2M+H)^+$, 471 $(M+H)^+$, 325 $(S)^+$, 147 $(BH_2)^+$, 105 $(C_6H_5CO)^+$; FAB<0 (matrix GT) m/z 469 $(M-H)^-$, 145 $(B)^-$, 121 $(C_6H_5CO_2)^-$; $[\alpha]_D^{20}$=−271 (c, 0,90 DMSO); Anal $C_{23}H_{19}FN_2O_6S$ (C, H, N, F).

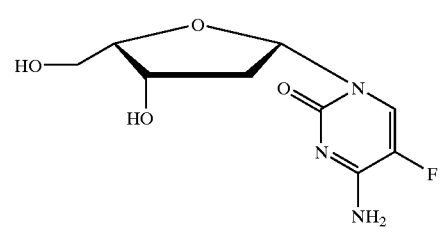

1-(2-Deoxy-β-L-threo-pento furanosyl)-5-fluorocytosine

A solution of this 4-thio intermediate 6 (1.0 g, 2.13 mmol) in methanolic ammonia (previously saturated at −10° C. and tightly stopped) (60 mL) was heated at 100° C. in a stainless-steel bomb for 3 h and then cooled to 0° C. The solution was evaporated to dryness under reduced pressure and the residue co-evaporated several times with methanol. The crude material was dissolved in water and the resulting solution was washed four times with methylene chloride. The aqueous layer was evaporated under reduced pressure and the residue was purified by silica gel column chromatography [eluent: stepwise gradient of methanol (3–20%) in methylene chloride]. Finally, the appropriate fractions were evaporated under reduced pressure, diluted with methanol and filtered through a unit Millex HV-4 (0.45 μm, Millipore) to provide 0.44 g of 7 (84% yield) which was crystallized from an ethyl acetate/methanol mixture; mp=199–201° C.; UV (ethanol): $\lambda_{max}$=226 nm (ε=7700), 281 nm (ε=8500), $\lambda_{min}$=262 nm (ε=6300); $^1$H-NMR (DMSO-d$_6$): δ7.99 (d, 1H, H-6, $J_{6\text{-}F5}$=7.4 Hz), 7.7–7.4 (br d, 2H, NH$_2$), 5.98 (d, 1H, H-1', $J_{1'\text{-}2'}$=8.1 Hz), 5.25 (d, 1H, OH-3', $J_{OH\text{-}3'}$=3.4 Hz), 4.71 (t, 1H, OH-5', $J_{OH\text{-}5'}$=$J_{OH\text{-}5''}$=5.6 Hz), 4.2 (m, 1H, H-3'), 3.8–3.6 (m, 3H, H-4', H-5' and H-5"), 2.5 (m, 1H, H-2'), 1.8 (m, 1H, H-2"); MS: FAB>0 (matrix GT) m/z 491 (2M+H)$^+$, 246 (M+H)$^+$, 130 (BH$_2$)$^+$; FAB<0 (matrix GT) m/z 489 (2M–H)$^+$, 244 (M–H)$^-$, 128 (B)$^-$; $[\alpha]_D^{20}$=–21 (c, 0.92 DMSO); Anal C$_9$H$_{12}$FN$_3$O$_4$ (C, H, N, F).

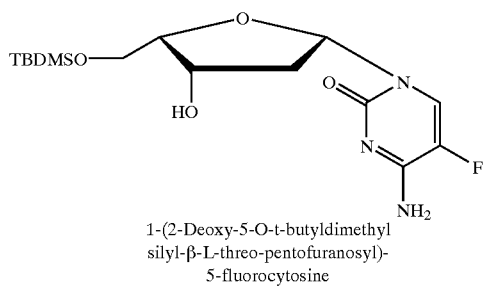

1-(2-Deoxy-5-O-t-butyldimethyl silyl-β-L-threo-pentofuranosyl)-5-fluorocytosine

To a solution of 7 (1.69 g, 6.89 mmol) in dry pyridine (35 mL) was added dropwise under argon atmosphere t-butyldimethylsilyl chloride (1.35 g, 8.96 mmol) and the mixture was stirred for 5 h at room temperature. Then the mixture was poured onto a saturated aqueous sodium hydrogen carbonate solution (100 mL) and extracted with chloroform (3×150 mL). Combined extracts were washed with water (2×200 mL) and then dried over sodium sulphate and evaporated under reduced pressure. The residue was purified by silica gel column chromatography [eluent: stepwise gradient of methanol (2–10%) in methylene chloride] to give pure 8 (2.94 g, 87%), as a white solid: mp 177–179° C.; UV (ethanol): $\lambda_{max}$ 241 nm (ε9900), 282 nm (ε10000), $\lambda_{min}$ 226 nm (ε8200), 263 nm (ε7600); $^1$H NMR (DMSO-d$_6$): δ7.95 (d, 1H, H-6, $J_{6\text{-}F5}$=7.3 Hz), 7.8–7.3 (br d, 2H, NH$_2$), 6.00 (dd, 1H, H-1', $J_{1'\text{-}2'}$=6.1 Hz and $J_{1'\text{-}2''}$=1.9 Hz), 5.3 (br s, 1H, OH-3'), 4.2 (br s, 1H, H-3'), 3.9–3.7 (m, 3H, H-4', H-5' and H-5"), 2.5 (m, 1H, H-2'), 1.81 (br d, 1H, H-2", J=14.6 Hz), 0.86 (s, 9H, (CH$_3$)$_3$C—Si), 0.05 (s, 6H, (CH$_3$)$_2$Si); MS (matrix GT): FAB>0 m/z 719 (2M+H)$^+$, 360 (M+H)$^+$, 130 (BH$_2$)$^+$, 115 (TBDMS)$^+$; FAB<0 m/z 717 (2M–H)$^-$, 358 (M–H)$^-$, 128 (B)$^-$; $[\alpha]_D^{20}$=–23 (c, 0.96 DMSO).

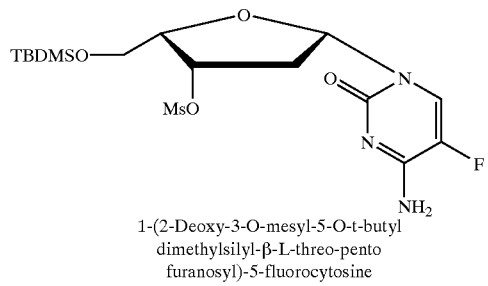

1-(2-Deoxy-3-O-mesyl-5-O-t-butyl dimethylsilyl-β-L-threo-pento furanosyl)-5-fluorocytosine A suspension of 8 (0.70 g, 1.96 mmol) in dry pyridine (30 mL) was stirred under argon and cooled to 0° C. Methanesulfonyl chloride (MsCl, 0.46 mL, 5.88 mmol) was added dropwise and the reaction mixture stirred at 0° C. for 5 h. Then the mixture was poured onto ice/water (100 mL) and extracted with chloroform (3×100 mL). Combined extracts were washed with a 5% aqueous sodium hydrogen carbonate solution (100 mL), with water (2×100 mL), dried over sodium sulphate and evaporated under reduced pressure. The resulting residue was purified by silica gel column chromatography [eluent: stepwise gradient of methanol (8–12%) in toluene] to give pure 9 (0.56 g, 65%) as a white solid: mp 83–84° C.; UV (ethanol): $\lambda_{max}$ 242 nm (ε8500), 282 nm (ε8800), $\lambda_{min}$ 225 nm (ε6400), 264 nm (ε6300); $^1$H NMR (DMSO-d$_6$): δ7.8–7.3 (br d, 2H, NH$_2$), 7.60 (d, 1H, H-6, $J_{6\text{-}F5}$=7.0 Hz), 5.93 (dd, 1H, H-1', $J_{1'\text{-}2'}$=4.5 Hz and $J_{1'\text{-}2''}$=2.0 Hz), 5.2 (m, 1H, H-3'), 4.1 (m, 1H, H-4'), 3.9–3.7 (m, 2H, H-5' and H-5"), 3.17 (s, 3H, CH$_3$SO$_2$), 2.7 (m, 1H, H-2'), 2.1 (m, 1H, H-2"), 0.99 (s, 9H, (CH$_3$)$_3$C—Si), 0.05 (s, 6H, (CH$_3$)$_2$Si); MS (matrix GT): FAB>0 m/z 875 (2M+H)$^+$, 438 (M+H)$^+$, 342 (M—CH$_3$SO$_3$)$^+$, 130 (BH$_2$)$^+$; FAB<0 m/z 873 (2M–H)$^-$, 436 (M–H)$^-$, 128 (B)$^-$, 95 (CH$_3$SO$_3$)$^-$; $[\alpha]_D^{20}$=–28 (c, 0.96 DMSO).

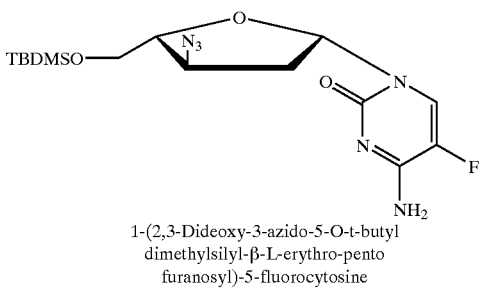

1-(2,3-Dideoxy-3-azido-5-O-t-butyl dimethylsilyl-β-L-erythro-pento furanosyl)-5-fluorocytosine To a solution of 9 (520 mg, 1.19 mmol) in anhydrous dimethylformamide (12 mL) was added lithium azide moistened with 10% methanol (300 mg, 5.31 mmol). The reaction mixture was stirred at 100° C. during 2.5 h, and then cooled to room temperature, poured onto ice/water (200 mL) and extracted with chloroform (3×100 mL). Combined extracts were washed with saturated aqueous sodium hydrogen carbonate solution (2×100 mL), with water (5×100 mL), and then dried over sodium sulphate and evaporated under reduced pressure. The residue was purified by silica gel column chromatography [eluent: methanol (4%) in chloroform] to give pure 10 (327 mg, 72%), which was crystallized from a diethyl ether/methanol mixture: mp 146–147° C.; UV (ethanol): $\lambda_{max}$ 243 nm (ε8700), 283 nm (ε8400), $\lambda_{min}$ 226 nm (ε7200), 264 nm (ε6700); $^1$H NMR (DMSO-d$_6$): δ7.90 (d, 1H, H-6, $J_{6\text{-}F5}$=7.0 Hz), 7.8–7.5 (br d, 2H, NH$_2$), 6.0 (m, 1H, H-1'), 4.3 (m, 1H, H-3'), 3.9–3.7 (m, 3H, H-4', H-5' and H"-5), 2.4–2.2 (m, 2H, H-2' and H-2"), 0.87 (s, 9H, (CH$_3$)$_3$C—Si), 0.05 (s, 6H, (CH$_3$)$_2$Si); MS (matrix GT): FAB>0 m/z 769 (2M+H)$^+$, 385 (M+H)$^+$, 130 (BH$_2$)$^+$; FAB<0 m/z 383 (M–H)$^-$; [α]$_D^{20}$=–67 (c, 0.96 DMSO).

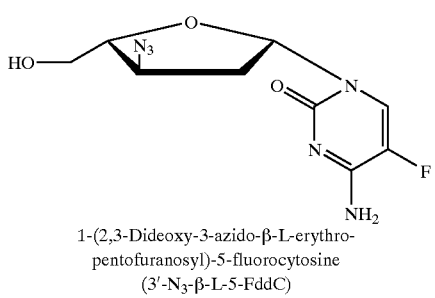

1-(2,3-Dideoxy-3-azido-β-L-erythro-
pentofuranosyl)-5-fluorocytosine
(3'-N$_3$-β-L-5-FddC)

A 1 M solution of tetrabutylammonium trifluoride in tetrahydrofurane (TBAF/THF, 1.53 mL, 1.53 mmol) was added to a solution of 10 (295 mg, 0.67 mmol) in anhydrous THF (4 mL). The resulting mixture was stirred at room temperature for 1.5 h and evaporated under reduced pressure. The residue was purified by silica gel column chromatography [eluent: stepwise gradient of methanol (4–8%) in chloroform]. Finally, the appropriate fractions were evaporated under reduced pressure, diluted with methanol and filtered through a unit Millex HV-4 (0.45 μm, Millipore) to give pure 11 (199 mg, 96%), which was crystallized from ethanol: mp 188–189° C. (lit.: mp 164–166° C. for the D-enantiomer); UV (ethanol): λmax 243 nm (ε8700), 283 nm (ε8100), λmin 226 nm (ε7100), 264 nm (ε6500); $^1$H NMR (DMSO-d$_6$): δ8.08 (d, 1H, H-6, J$_{6-F5}$=7.3 Hz), 7.8–7.5 (br d, 2H, NH$_2$), 6.0 (m, 1H, H-1'), 5.3 (br s, 1H, OH-5'), 4.4 (m, 1H, H-3'), 3.8 (m, 1H, H-4'), 3.7–3.5 (m, 2H, H-5' and H-5"), 2.3 (m, 2H, H-2' and H-2"); MS (matrix GT): FAB>0 m/z 811 (3M+H)$^+$, 725 (2M+2G+H)$^+$, 633 (2M+G+H)$^+$, 541 (2M+H)$^+$, 363 (M+G+H)$^+$, 271 (M+H)$^+$, 142 (S)$^+$, 130 (BH$_2$)$^+$; FAB<0 m/z 647 (2M+T–H)$^-$, 539 (2M–H)$^-$, 377 (M+T–H)$^-$, 269 (M–H)$^-$, 128 (B)$^-$; [α]$_D^{20}$=–31 (c, 0.90 DMSO); Anal. (C$_9$H$_{11}$FN$_6$O$_3$) C, H, N, F.

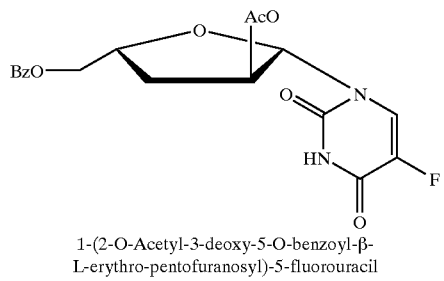

1-(2-O-Acetyl-3-deoxy-5-O-benzoyl-β-
L-erythro-pentofuranosyl)-5-fluorouracil

A suspension of 5-fluorouracil (5.15 g, 39.6 mmol) was treated with hexamethyldisilazane (HMDS, 257 mL) and a catalytic amount of ammonium sulfate during 18 h under reflux. After cooling to room temperature, the mixture was evaporated under reduced pressure, and the residue obtained as a colourless oil was diluted with anhydrous 1,2-dichloroethane (290 mL). To the resulting solution was added 1,2-di-O-acetyl-3-deoxy-5-O-benzoyl-L-erythro-pentofuranose 12 (8.5 g, 26.4 mmol) [Ref.: Mathé, C., Ph.D. Dissertation, Université de Montpellier II—Sciences et Techniques du Languedoc, Montpellier (France), Sep. 13, 1994; Gosselin, G.; Mathé, C.; Bergogne, M.-C.; Aubertin, A. M.; Kirn, A.; Sommadossi, J. P.; Schinazi, R. F.; Imbach, J. L., "2'- and/or 3'-deoxy-β-L-pentofuranosyl nucleoside derivatives: stereospecific synthesis and antiviral activities," *Nucleosides & Nucleotides*, 1994, 14 (3–5), 611–617] in anhydrous 1,2-dichloroethane (120 mL), followed by addition of trimethylsilyl trifluoromethanesulfonate (TMSTf, 9.6 mL, 52.8 mmol). The solution was stirred for 5 h at room temperature under argon atmosphere, then diluted with chloroform (200 mL), washed with the same volume of a saturated aqueous sodium hydrogen carbonate solution and finally with water (2×300 mL). The organic phase was dried over sodium sulphate, then evaporated under reduced pressure. The resulting crude material was purified by silica gel column chromatography [eluent: stepwise gradient of methanol (0–6%) in methylene chloride] to give pure 13 (8.59 g, 83%), which was crystallized from toluene: mp 65–68° C.; UV (ethanol): λ$_{max}$ 228 nm (ε11200) 268 nm (ε14000),λ$_{min}$ 242 nm (ε7800); $^1$H NMR (DMSO-d$_6$): δ11.9

Analytical data

| Compound | Formula | Anal Calculated | | | | Anal Found | | | |
| --- | --- | --- | --- | --- | --- | --- | --- | --- | --- |
| | | C | H | N | F | C | H | N | F |
| 2 | C$_{25}$H$_{21}$FN$_2$O$_9$ | 58.59 | 4.13 | 5.47 | 3.71 | 58.33 | 4.25 | 4.24 | 3.49 |
| 5 | C$_{23}$H$_{19}$FN$_2$O$_7$ | 60.79 | 4.21 | 6.17 | 4.18 | 61.22 | 4.26 | 6.18 | 3.90 |
| 6 | C$_{23}$H$_{19}$FN$_2$O$_6$S | 58.71 | 4.07 | 5.96 | 4.04 | 58.25 | 4.10 | 5.91 | 4.00 |
| 7 | C$_9$H$_{12}$FN$_3$O$_4$ | 44.08 | 4.87 | 17.17 | 7.75 | 43.87 | 5.13 | 16.81 | 7.42 |
| 11 | C$_9$H$_{11}$FN$_6$O$_3$ | 40.00 | 4.10 | 31.10 | 7.03 | 40.35 | 3.83 | 31.38 | 7.12 |

EXAMPLE 2

Preparation of β-L-(2'-azido)-2',3'-dideoxy-5-
fluorocytidine

General procedures and instrumentation used have been described in Example 1 in the Experimental protocols part of the synthesis of the 3' isomer (3'-N$_3$-β-L-FddC).

(br s, 1H, NH), 8.0–7.5 (m, 6H, C$_6$H$_5$CO and H-6), 5.8 (m, 1H, H-1'), 5.3 (m, 1H, H-2'), 4.6–4.5 (m, 3H, H-4', H-5' and H-5"), 2.4–2.3 (m, 1H, H-3'), 2.1–2.0 (m, 4H, H-3" and CH$_3$CO); MS (matrix GT): FAB>0 m/z 393 (M+H)$^+$, 263 (S)$^+$, 105 (C$_6$H$_5$CO)$^+$; FAB<0 m/z 391 (M–H)$^-$, 331 (M–[CH$_3$CO$_2$H]–H)$^-$, 129 (B)$^-$, 121 (C$_6$H$_5$CO$_2$)$^-$; [α]$_D^{20}$=–8 (c,1.00 DMSO); Anal. (C$_{18}$H$_{17}$FN$_2$O$_7$; 2/3 C$_7$H$_8$) C, H, N, F.

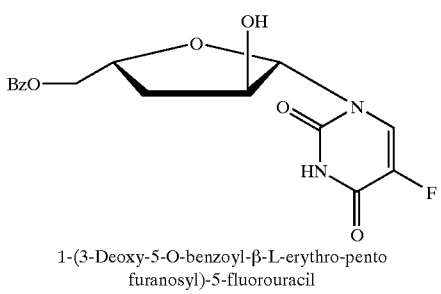

1-(3-Deoxy-5-O-benzoyl-β-L-erythro-pento
furanosyl)-5-fluorouracil

To a solution of 13 (5.90 g, 15.0 mmol) in tetrahydrofuirane (THF, 175 mL), was added sodium methoxide (2.84 g, 52.6 mmol). The resulting suspension was stirred at room temperature during 5 h and then neutralized by addition of Dowex 50 W×2 (H$^+$ form). The resin was filtered and washed with warm methanol, and the combined filtrates were evaporated to dryness. Column chromatography of the residue on silica gel [eluent: stepwise gradient of methanol (0–8%) in methylene chloride] afforded 14 (4.11 g, 78%), which was crystallized from a methylene chloride/methanol mixture: mp 154–156° C.; UV (ethanol): $\lambda_{max}$ 226 nm (ε23000), 268 nm (ε16000), $\lambda_{min}$ 246 nm (ε8900); $^1$H NMR (DMSO-d$_6$): δ11.8 (br s, 1H, NH), 8.0–7.5 (m, 6H, C$_6$H$_5$CO and H-6), 5.6 (br s, 2H, H-1' and OH-2'), 4.5 (m, 3H, H-4', H-5' and H-5"), 4.3 (m, 1H, H-2'), 2.1–2.0 (m, 1H, H-3'), 1.9 (m, 1H, H-3"); MS (matrix GT): FAB>0 m/z 701 (2M+H)$^+$, 351 (M+H)$^+$, 221 (S)$^+$, 131 (BH$_2$)$^+$, 105 (C$_6$H$_5$CO)$^+$; FAB<0 m/z 1049 (3M-H)$^-$, 699 (2M-H)$^-$, 441 (M+G-H)$^-$, 349 (M-H)$^-$, 129 (B)$^-$, 121 (C$_6$H$_5$CO$_2$)$^-$; $[\alpha]_D^{20}$=−3 (c, 1.04 DMSO); Anal. (C$_{16}$H$_{15}$FN$_2$O$_6$) C, H, N, F.

1-(3-Deoxy-5-O-benzoyl-β-L-threo-pentofuranosyl)-
5-fluorouracil 15

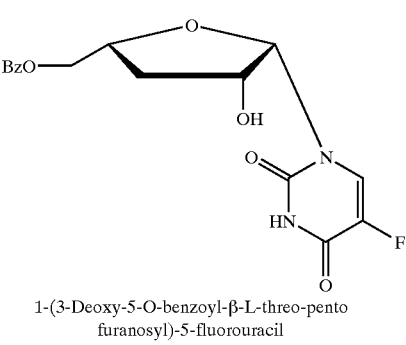

1-(3-Deoxy-5-O-benzoyl-β-L-threo-pento
furanosyl)-5-fluorouracil

Dicyclohexylcarbodiimide (DCC, 3.53 g, 17.1 mmol) and dichloroacetic acid (0.235 mL, 2.56 mmol) were added to a solution of 14 (2.00 g, 5.71 mmol) in anhydrous benzene (50 mL), DMSO (35 mL) and pyridine (0.46 mL). The resulting solution was stirred at room temperature under argon during 4 h and diluted with ethyl acetate (300 mL). Oxalic acid (1.54 g, 17.1 mmol) dissolved in methanol (4.6 mL) was added and the reaction mixture was stirred at room temperature during 1 h and then filtered to eliminate precipitated dicyclohexylurea (DCU). The filtrate was washed with brine (3×300 mL), with a saturated aqueous sodium hydrogen carbonate solution (2×300 mL) and finally with water (3×200 mL) before being dried over sodium sulphate and evaporated under reduced pressure. The resulting residue was co-evaporated several times with absolute ethanol and dissolved in a mixture of absolute ethanol (31 mL) and anhydrous benzene (15 mL). The resulting solution was then cooled to 0° C. and sodium borohydride (NaBH$_4$, 0.32 g, 8.56 mmol) was added. The reaction mixture was stirred at room temperature under argon during 1 h and diluted with ethyl acetate (300 mL) filtered. The filtrate was washed with a saturated aqueous sodium chloride solution (3×300 mL) and with water (2×200 mL) before being dried over sodium sulphate and evaporated under reduced pressure. The resulting residue was purifiedby silica gel column chromatography [eluent: stepwise gradient of methanol (0–6%) in chloroform] to give pure 15 (1.10 g, 55%), as a white foam: mp 171–172° C.; UV (ethanol): $\lambda_{max}$ 228 nm (ε14700) 270 nm (ε9100), $\lambda_{min}$ 248 nm (ε5000); $^1$H NMR (DMSO-d$_6$): δ11.8 (br s, 1H, NH), 8.0–7.5 (m, 6H, C$_6$H$_5$CO and H-6), 5.90 (dd, 1H, H-1', J$_{1'-2'}$=4.1 Hz and J$_{1'-F5}$=1.8 Hz), 5.5 (br s, 1H, OH-2'), 4.7 (br q, 1H, H-4', J=11.7 Hz and J=7.0 Hz), 4.4–4.3 (m, 3H, H-2', H-5' and H-5"), 2.4 (m, 1H, H-3'), 1.9–1.8 (m, 1H, H-3"); MS (matrix GT): FAB>0 m/z 701 (2M+H)$^+$, 351 (M+H)$^+$, 221 (S)$^+$, 131 (BH$_2$)$^+$, 105 (C$_6$H$_5$CO)$^+$; FAB<0 m/z 1049 (3M-H)$^-$, 699 (2M-H)$^-$, 349 (M-H)$^-$, 129 (B)$^-$, 121 (C$_6$H$_5$CO$_2$)$^-$; $[\alpha]_D^{20}$=−101 (c, 0.70 DMSO)

1-(2O-Acetyl-3-deoxy-5-O-benzoyl-β-L-threo-
pentofuranosyl)-5-fluorouracil 16

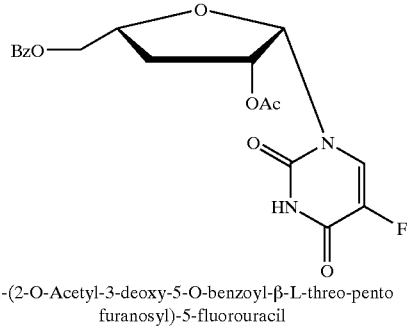

1-(2-O-Acetyl-3-deoxy-5-O-benzoyl-β-L-threo-pento
furanosyl)-5-fluorouracil

Acetic anhydride (0.88 mL, 9.28 mmol) was added under argon to a solution of 15 (2.50 g, 7.14 mmol) in dry pyridine (50 mL) and the resulting mixture was stirred at room temperature for 22 h. Then, ethanol was added and the solvents were evaporated under reduced pressure. The residue was purified by silica gel column chromatography [eluent: stepwise gradient of methanol (0–2%) in methylene chloride] to give pure 16 (2.69 g, 96%) as a white foam; mp=68–70° C. (foam); UV (ethanol): $\lambda_{max}$=239 nm (ε=15000) 267 nm (ε=8800), $\lambda_{min}$=248 nm (ε=5600); $^1$H NMR (DMSO-d$_6$): δ ppm 11.9 (br s, 1H, NH), 8.1–7.5 (m, 6H, C$_6$H$_5$CO and H-6), 6.10 (d, 1H, H-1', J$_{1'-2'}$=4.3 Hz), 5.4 (m, 1H, H-2'), 4.6–4.4 (m, 3H, H-4', H-5' and H-5"), 2.6 (m, 1H, H-3'), 2.03 (m, 1H, H-3"), 1.86 (s, 3H, CH$_3$CO); MS (matrix GT): FAB>0 m/z 785 (2M+H)$^+$, 393 (M+H)$^+$, 263 (S)$^+$, 131 (BH$_2$)$^+$, 105 (C$_6$H$_5$CO)$^+$; 43 (CH$_3$CO)$^+$; FAB<0 m/z 391 (M-H)$^-$, 129 (B)$^-$, 121 (C$_6$H$_5$CO$_2$)$^-$, 59 (CH$_3$CO$_2$)$^-$; $[\alpha]_D^{20}$=−81 (c, 0.95 DMSO).

1-(2-O-Acetyl-3-deoxy-5-O-benzoyl-β-L-threo-pentofuranosyl)-4-thio-5-fluorouracil 17

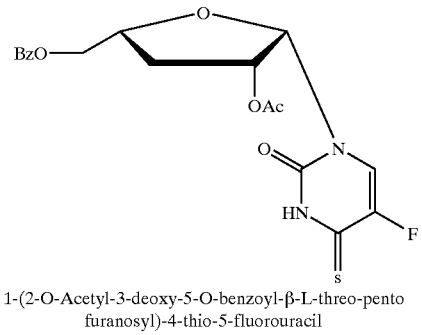

1-(2-O-Acetyl-3-deoxy-5-O-benzoyl-β-L-threo-pento furanosyl)-4-thio-5-fluorouracil Lawesson's reagent (1.9 g, 4.69 mmol) was added under argon to a solution of 16 (2.63 g, 6.70 mmol) in anhydrous 1,2-dichloroethane (165 mL) and the reaction mixture was stirred overnight under reflux. The solvent was then evaporated under reduced pressure and the residue was purified by silica gel column chromatography [eluent: stepwise gradient of methanol (0–3%) in methylene chloride] to give the 4-thio derivative 17 (2.65 g, 96% yield) as a yellow foam; mp=78–79° C. (foam); UV (ethanol): $\lambda_{max}$=230 nm (ε=15900) 334 nm (ε=15600), $\lambda_{min}$=288 nm (ε=3200); $^1$H NMR (DMSO-d$_6$): δ ppm 13.2 (br s, 1H, NH), 8.1–7.5 (m, 6H, C$_6$H$_5$CO and H-6), 6.08 (d, 1H, H-1', $J_{1'-2'}$=4.3 Hz), 5.4 (m, 1H, H-2'), 4.7–4.4 (m, 3H, H-4', H-5' and H-5"), 2.6 (m, 1H, H-3'), 2.0 (m, 1H, H-3"), 1.84 (s, 3H, CH$_3$CO); MS (matrix GT): FAB>0 m/z 409 (M+H)$^+$, 263 (S)$^+$, 147 (BH$_2$)$^+$, 105 (C$_6$H$_5$CO)$^+$, 43 (CH$_3$CO)$^+$; FAB<0 m/z 407 (M–H)$^-$, 145 (B)$^-$, 121 (C$_6$H$_5$CO$_2$)$^-$, 59 (CH$_3$CO$_2$)$^-$; $[\alpha]_D^{20}$=–155 (c, 1.00 DMSO).

1-(3-Deoxy-β-L-threo-pentofuranosyl)-5-fluorocytosine 18

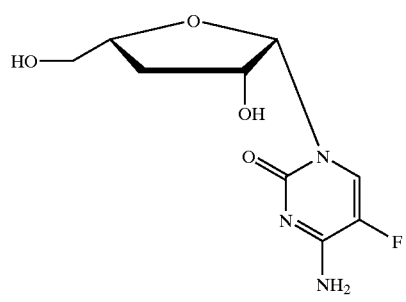

1-(3-Deoxy-β-L-threo-pento furanosyl)-5-fluorocytosine

A solution of the 4-thio derivative 17 (0.86 g, 2.19 mmol) in methanolic ammonia (previously saturated at –10° C. and tightly stopped) (44 mL) was heated at 100° C. in a stainless-steel bomb for 3 h and then cooled to 0° C. The solution was evaporated to dryness under reduced pressure and the residue co-evaporated several times with methanol. The crude material was dissolved in water and the resulting solution was washed four times with methylene chloride. The aqueous layer was evaporated under reduced pressure and the residue was purified by silica gel column chromatography [eluent: stepwise gradient of methanol (3–12%) in chloroform]. Finally, the appropriate fractions were evaporated under reduced pressure, diluted with methanol and filtered through a unit Millex HV-4 (0.45 μm, Millipore) to provide 0.46 g of 18 (86% yield) which was crystallized from a methylene/methanol mixture; mp=137–138° C.; UV (ethanol): $\lambda_{max}$=240 nm (ε=8300) 284 nm (ε=8100), $\lambda_{min}$=226 nm (ε=7300) 263 nm (ε=5500); $^1$H NMR (DMSO-d$_6$): δ ppm 8.34 (d, 1H, H-6, $J_{6-F5}$=7.5 Hz), 7.7–7.4 (br pd, 2H, NH$_2$), 5.83 (dd, 1H, H-1', $J_{1'-2'}$=4,4 Hz, $J_{1'-F5}$=1.9 Hz), 5.22 (d, 1H, OH-2', $J_{OH-2'}$=5.1 Hz), 5.15 (t, 1H, OH-5', $J_{OH-5'}$=$J_{OH-5''}$=4.8 Hz), 4.3 (m, 1H, H-2'), 4.0 (m, 1H, H-4'), 3.6–3.5 (m, 2H, H-5' and H-5") 2.2 (m, 1H, H-3'), 1.7 (m, 1H, H-3"); MS (matrix GT): FAB>0 m/z 491 (2M+H)$^+$, 246 (M+H)$^+$, 130 (BH$_2$)$^+$; FAB<0 m/z 244 (M–H)$^-$, 128 (B)$^-$; $[\alpha]_D^{20}$=–135 (c, 0.89 DMSO). Elemental analysis, C$_9$H$_{12}$FN$_3$O$_4$, ½H$_2$O; Calc. C=42.52; H=5.15; N=16.53; F=7.47; Found: C=43.16; H=5.32; N=16.97 ; F=6.92

1-(3-Deoxy-5-O-t-butyldimethylsilyl-β-L-threo-pentofuranosyl)-5-fluorocytosine 19

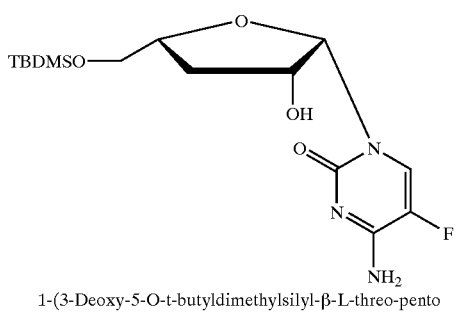

1-(3-Deoxy-5-O-t-butyldimethylsilyl-β-L-threo-pento furanosyl)-5-fluorocytosine

To a solution of 18 (1.38 g, 5.63 mmol) in dry pyridine (30 mL) was added dropwise under argon atmosphere t-butyldimethylsilyl chloride (1.10 g, 7.32 mmol) and the mixture was stirred for 10 h at room temperature. Then the mixture was poured onto a saturated aqueous sodium hydrogen carbonate solution (100 mL) and extracted with chloroform (3×150 mL). Combined extracts were washed with water (2×200 mL) and then dried over sodium sulphate and evaporated under reduced pressure. The residue was purified by silica gel column chromatography [eluent: stepwise gradient of methanol (2–10%) in methylene chloride] to give pure 19 (1.74 g, 86% yield) as a white solid: mp 202–204° C.; UV (ethanol): $\lambda_{max}$ 241 nm (ε7800), 284 nm (ε7800), $\lambda_{min}$ 226 nm (ε6600), 263 nm (ε5400); $^1$H NMR (DMSO-d$_6$): δ7.77 (d, 1H, H-6, $J_{6-F5}$=7.1 Hz), 7.7–7.3 (br d, 2H, NH$_2$), 6.88 (dd, 1H, H-1', $J_{1'-2'}$=4.9 Hz and $J_{1'-F5}$=1.9 Hz), 5.24 (d, 1H, OH-3', $J_{OH-3'}$=4.6 Hz), 4.4 (m, 1H, H-2'), 4.0 (m, 1H, H-4'), 3.8–3.7 (m, 2H, H-5' and H-5"), 2.2 (m, 1H, H-3'), 1.7 (m, 1H, H-3"), 0.84 (s, 9H, (CH$_3$)$_3$C—Si), 0.06 (s, 6H, (CH$_3$)$_2$Si); MS (matrix GT): FAB>0 m/z 1437 (4M+H)$^+$, 1078 (3M+H)$^+$, 719 (2M+H)$^+$, 360 (M+H)$^+$, 231 (S)$^+$, 130 (BH$_2$)$^+$, 115 (TBDMS)$^+$; FAB<0 m/z 1076 (3M–H)$^-$, 717 (2M–H)$^-$, 358 (M–H)$^-$, 128 (B)$^-$; $[\alpha]_D^{20}$=–107 (c, 0.88 DMSO).

1-(3-Deoxy-2-O-mesyl-5-O-t-butyl-dimethylsilyl-β-L-threo-pentofuranosyl)-5-fluorocytosine 20

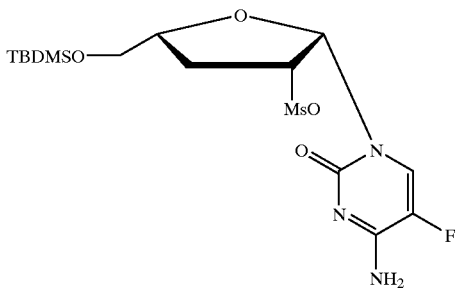

1-(3-Deoxy-2-O-mesyl-5-O-t-butyl-dimethylsilyl-β-L-threo-pentofuranosyl)-5-fluorocytosine A suspension of 19 (1.70 g, 4.73 mmol) in dry pyridine (80 mL) was stirred under argon and cooled to 0° C. Methanesulfonyl chloride (MsCl, 1.21 mL, 15.6 mmol) was added dropwise and the reaction mixture stirred at 0° C. for 5 h. Then the mixture was poured onto ice/water (300 mL) and extracted with chloroform (3×300 mL). Combined extracts were washed with a 5% aqueous sodium hydrogen carbonate solution (300 mL), with water (2×300 mL) and then dried over sodium sulphate and evaporated under reduced pressure. The resulting residue was purified by silica gel column chromatography [eluent: stepwise gradient of methanol (8–12%) in toluene] to give pure 20 (1.41 g, 68% yield) as a white solid: mp 75–76 ° C.; UV (ethanol): $\lambda_{max}$ 243 nm (ε8100), 282 nm (ε7300), $\lambda_{min}$ 225 nm (ε6000), 265 nm (ε6000); $^1$H NMR (DMSO-$d_6$): δ7.9–7.6 (br d, 2H, $NH_2$), 7.85 (d, 1H, H-6, $J_{6\text{-}F5}$=7.0 Hz), 6.08 (dd, 1H, H-1', $J_{1'\text{-}2'}$=5.2 Hz and $J_{1'\text{-}F5}$=1.6 Hz), 5.4 (m, 1H, H-2'), 4.1 (m, 1H, H-4'), 3.9 (m, 1H, H-5'), 3.7 (m, 1H, H-5"), 3.11 (s, 3H, $CH_3SO_2$), 2.47 (m, 1H, H-3'), 2.0 (m, 1H, H-2"), 0.85 (s, 9H, $(CH_3)_3C$—Si), 0.05 (s, 6H, $(CH_3)_2Si$); MS (matrix GT): FAB>0 m/z 1312 (3M+H)$^+$, 875 (2M+H)$^+$, 438 (M+H)$^+$, 309 (S)$^+$, 130 ($BH_2$)$^+$; FAB<0 m/z 1310 (2M–H)$^-$, 873 (2M–H)$^-$, 436 (M–H)$^-$, 128 (B)$^-$, 95 ($CH_3SO_3$)$^-$; $[\alpha]_D^{20}$=−84 (c, 0.84 DMSO).

1-(2,3-Dideoxy-2-azido-5-O-t-butyldimethylsilyl-β-L-erythro-pentofuranosyl)-5-fluorocytosine 21

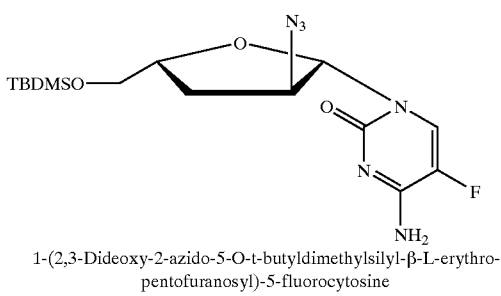

1-(2,3-Dideoxy-2-azido-5-O-t-butyldimethylsilyl-β-L-erythro-pentofuranosyl)-5-fluorocytosine To a solution of 20 (442 mg, 1.01 mmol) in anhydrous dilmethylformamide (12 mL) was added lithium azide moistened with 10% methanol (265 mg, 4.87 mmol). The reaction mixture was stirred at 100° C. during 2.5 h, and then cooled to room temperature, poured onto ice/water (200 mL) and extracted with chloroform (3×100 mL). Combined extracts were washed with a saturated aqueous sodium hydrogen carbonate solution (2×100 mL), with water (5×100 mL) and then dried over sodium sulphate and evaporated under reduced pressure. The residue was purified by silica gel column chromatography [eluent: methanol (4%) in chloroform] to give pure 21 (291 mg, 75% yield) as a white solid: mnp 147–148° C.; UV (ethanol): $\lambda_{max}$ 242 nm (ε7700), 283 nm (ε7400), $\lambda_{min}$ 226 nm (ε6600), 264 nm (ε5800); $^1$H NMR (DMSO-$d_6$): δ8.05 (d, 1H, H-6, $J_{6\text{-}F5}$=7.0 Hz), 7.9–7.4 (br d, 2H, $NH_2$), 5.7 (br s, 1H, H-1'), 4.37 (d, 1H, H-2', $J_{2'\text{-}3'}$=5.5 Hz), 4.3 (m, 1H, H-4'), 4. (m, 1H, H-5'), 3.7 (m, 1H,H-5"), 2.0 (m, 1H, H-3'), 1.8 (m, 1H, H-3"), 0.88 (s, 9H, $(CH_3)_3C$—Si), 0.05 (s, 6H, $(CH_3)_2Si$); MS (matrix GT): FAB>0 m/z 769 (2M+H)$^+$, 385 (M+H)$^+$, 130 ($BH_2$)$^+$; FAB<0 m/z 1151 (3M–H)$^-$, 767 (2M–H)$^-$, 383 (M–H)$^-$, 128 (B)$^-$; $[\alpha]_D^{20}$=+25 (c, 0.95 DMSO).

1-(2,3-Dideoxy-2-azido-β-L-erythro-pentofuranosyl)-5-fluorocytosine 22 (2'-$N_3$-β-L-5-FddC)

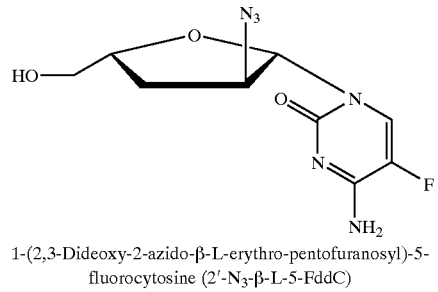

1-(2,3-Dideoxy-2-azido-β-L-erythro-pentofuranosyl)-5-fluorocytosine (2'-$N_3$-β-L-5-FddC)

A 1 M solution of tetrabutylammonium trifluoride in tetrahydrofurane (TBAF/THF, 1.90 mL, 1.90 mmol) was added to a solution of 21 (480 mg, 1.25 mmol) in anhydrous THF (8 mL). The resulting mixture was stirred at room temperature for 1.5 h and evaporated under reduced pressure. The residue was purified by silica gel column chromatography [eluent: stepwise gradient of methanol (4–8%) in chloroform]. Finally, the appropriate fractions were evaporated under reduced pressure, diluted with methanol and filtered through a unit Millex HV-4 (0.45 μm, Millipore) to give pure 22 (304 mg, 90% yield), which was crystallized from ethanol: mp 219–221° C.; UV (ethanol): $\lambda_{max}$ 241 nm (ε7700), 284 nm (ε7300), $\lambda_{min}$ 225 nm (ε6500), 263 nm (ε5400); $^1$H NMR (DMSO-$d_6$): δ8.31 (d, 1H, H-6, $J_{6\text{-}F5}$=7.4 Hz), 7.9–7.4 (br d, 2H, $NH_2$), 5.65 (m, 1H, H-1'), 5.32 (br s, 1H, OH-5'), 4.35 (d, 1H, H-2', $J_{2'\text{-}3'}$=5.6 Hz), 4.2 (m, 1H, H-4'), 3.8 (m, 1H, H-5'), 3.6 (m, 1H, H-5"), 2.1 (m, 1H, H-3'), 1.8 (m, 1H, H-2"); MS (matrix GT): FAB>0 m/z 541 (2M+H)$^+$, 363 (M+G+H)$^+$, 271 (M+H)$^+$, 130 ($BH_2$)$^+$; FAB<0 m/z 539 (2M–H)$^-$, 269 (M–H)$^-$, 128 (B)$^-$; $[\alpha]_D^{20}$=+29 (c, 0.85 DMSO); Anal. ($C_9H_{11}FN_6O_3$) C, H, N, F.

| | | Analytical data | | | | | | | |
|---|---|---|---|---|---|---|---|---|---|
| | | Anal. calculated | | | | Anal. found | | | |
| Compound | Formula | C | H | N | F | C | H | N | F |
| 13 | C$_{18}$H$_{17}$FN$_2$O$_7$, ⅔ C$_7$H$_8$ | 59.99 | 4.96 | 6.18 | 4.19 | 59.60 | 4.96 | 6.02 | 3.76 |
| 14 | C$_{16}$H$_{15}$FN$_2$O$_6$ | 54.86 | 4.32 | 8.00 | 5.42 | 54.75 | 4.16 | 7.78 | 5.49 |
| 22 | C$_9$H$_{11}$FN$_6$O$_3$ | 40.00 | 4.10 | 31.10 | 7.03 | 40.07 | 4.16 | 31.10 | 6.99 |

Anti-HBV Activity

The ability of β-L-(2' or 3'-azido)-2',3'-dideoxy-5-fluorocytosine compounds to inhibit the replication of HBV in a host can be evaluated according to any known method, including that below.

The antiviral evaluations were performed on two separate passages of cells, two cultures per passage (4 cultures total). All wells, in all plates, were seeded at the same density and at the same time.

Due to the inherent variations in the levels of both intracellular and extracellular HBV DNA, only depressions greater than 3.0-fold (for HBV virion DNA) or 2.5-fold (for HBV DNA replication intermediates) from the average levels for these HBV DNA forms in untreated cells are generally considered to be statistically significant [P<0.05] (Korba and Gerin, Antiviral Res. 19: 55–70, 1992). The levels of integrated HBV DNA in each cellular DNA preparation (which remain constant on a per cell basis in these experiments) were used to calculate the levels of intracellular HBV DNA forms, thereby eliminating technical variations inherent in the blot hybridization assays.

Typical values for extracellular HBV virion DNA in untreated cells range from 50 to 150 pg/ml culture medium (average of approximately 76 pg/ml). Intracellular HBV DNA replication intermediates in untreated cells range from 50 to 100 pg/ug cell DNA (average approximately 74 pg/ug cell DNA). In general, depressions in the levels of intracellular HBV DNA due to treatment with antiviral compounds are less pronounced, and occur more slowly, than depressions in the levels of HBV virion DNA.

For reference, the manner in which the hybridization analyses were performed for these experiments results in an equivalence of approximately 1.0 pg intracellular HBV DNA/ug cellular DNA to 2–3 genomic copies per cell and 1.0 pg of extracellular HBV DNA/ml culture medium to 3×10$^5$ viral particles/ml.

Toxicity analyses were performed in order to assess whether any observed antiviral effects were due to a general effect on cell viability. This can be assessed by the uptake of neutral red dye, a standard and widely used assay for cell viability in a variety of virus-host systems, including HSV (herpes simplex virus) and HIV.

The test compounds were used in the form of stock solutions in DMSO (frozen on dry ice). Daily aliquots of the test samples were made and frozen at −20° C. so that each individual aliquot would be subjected to a single freeze-thaw cycle. The daily test aliquots were thawed, suspended into culture medium at room temperature and immediately added to the cell cultures. The results are provided in Table 1.

TABLE 1

Anti-HBV Activity and Cytotoxicity of β-L-2'- and 3'-azido-5-FddC Compared to Lamivudine and L-5-FddC

| Compound | Transfected 2.2.15 cells EC$_{50}$ (μM) R.I. | Normal Hep G$_2$ cells CC$_{50}$ (μM) |
|---|---|---|
| L-2-azido-5-FddC | 0.1 | >200 |
| L-3-azido-5-FddC | 0.01 | >200 |
| L-5-FddC | 0.05 | >200 |
| Lamivudine (3TC) | 0.03 | >200 |

EXAMPLE 3
Toxicity of Compounds

The ability of the active compounds to inhibit the growth of virus in 2.2.15 cell cultures (HepG2 cells transformed with hepatitis virion) was evaluated. As illustrated in Table 1, no significant toxicity (greater than 50% depression of the dye uptake levels observed in untreated cells) was observed for any of the test compounds at the concentrations 100 mM.

Toxicity analyses were performed in 96-well flat bottomed tissue culture plates. Cells for the toxicity analyses were cultured and treated with test compounds with the same schedule as used for the antiviral evaluations. Each compound was tested at 4 concentrations, each in triplicate cultures. Uptake of neutral red dye was used to determine the relative level of toxicity. The absorbance of internalized dye at 510 nM (A$_{510}$) was used for the quantitative analysis. Values are presented as a percentage of the average A$_{510}$ values (±standard deviations) in 9 separate cultures of untreated cells maintained on the same 96-well plate as the test compounds. The percentage of dye uptake in the 9 control cultures on plate 40 was 100±3. At 150–190 μM β-D-ddC, a 2-fold reduction in dye uptake (versus the levels observed in untreated cultures) is typically observed in these assays (Korba and Gerin, Antiviral Res. 19: 55–70, 1992).

EXAMPLE 4
Effect of Anti-HBV β-L-deoxycytidine Analogues on Cell Growth as Assessed by Human Bone Marrow Clonogenic Assays The effects of anti-HBV β-L-deoxycytidine analogues on cell growth as assessed by human bone marrow clonogenic assays are shown in Table 2.

TABLE 2

| Compound | CFU-GM EC$_{50}$ | BFU-E EC$_{50}$ (μM) |
|---|---|---|
| L-2'-azido-5-FddC | >10 | >10 |
| L-3'-azido-5-FddC | 10 | 10 |
| L-5-FddC | 1.2 | 1.8 |
| Lamivudine (3TC) | >10 | >10 |

TABLE 2-continued

| Compound | CFU-GM EC$_{50}$ | BFU-E EC$_{50}$ ($\mu$M) |
|---|---|---|
| D-ddC (control) | 0.7 | 0.05 |
| Zidovudine (AZT) (control) | 1.9 | 0.6 |

Preparation of Pharmaceutical Compositions

The compounds disclosed herein and their pharmaceutically acceptable salts, prodrugs, and derivatives, are useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

Humans suffering from any of these conditions can be treated by administering to the patient an effective HBV-treatment amount of one or a mixture of the active compounds described herein or a pharmaceutically acceptable derivative or salt thereof, optionally in a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount without causing serious toxic effects in the patient treated.

A preferred dose of the active compound for all of the above-mentioned conditions will be in the range from about 1 to 60 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art. In one embodiment, the active compound is administered as described in the product insert or Physician's Desk Reference for 3'-azido-3'-deoxythymidine (AZT), 2',3'-dideoxyinosine (DDI), 2',3'-dideoxycytidine (DDC), or 2',3'-dideoxy-2',3'-didehydrothymidine (D4T) for HIV indication.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 mM, preferably about 1.0 to 10 mM. This may be achieved, for example, by the intravenous injection of a 0.1 to 5% solution of the active ingredient, optionally in saline, or administered as a bolus of the active ingredient.

The active compound can be provided in the form of pharmaceutically acceptable salts. As used herein, the term pharmaceutically acceptable salts or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

Modifications of the active compound, specifically at the $N^6$ or $N^4$ and 5'-O positions, can affect the bioavailability and rate of metabolism of the active species, thus providing control over the delivery of the active species.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, water, chewing gum or the like. A syrup may contain, in addition to the active compounds, sucrose as a sweetening agent and certain preservatives, dyes and colorings and flavors.

The active compound, or pharmaceutically acceptable derivative or salt thereof can also be mixed with other active materials that do not impair the desired action, or with materials that supplement the desired action, such as antibiotics, antifungals, antiinflammatories, or other antivirals, including anti-HBV, anti-cytomegalovirus, or anti-HIV agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS). In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of the appended claims.

We claim:

1. A method for the treatment of hepatitis B virus infection in a host comprising administering an effective amount of a β-L-(2'-azido)-2',3'-dideoxy-5-fluorocytidine of the formula:

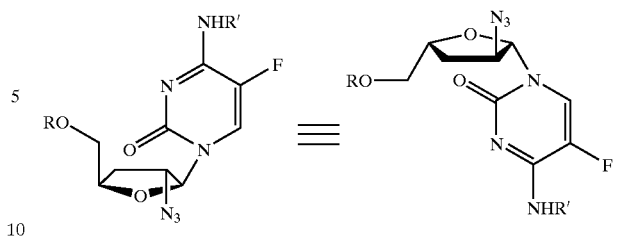

or a pharmaceutically acceptable ester, salt or prodrug thereof, wherein R is H, acyl, monophosphate, diphosphate, or triphosphate, or a stabilized phosphate derivative (to form a stabilized nucleotide prodrug), and R' is H, acyl, or alkyl.

2. The method of claim 1, wherein R is H.
3. The method of claim 1, wherein R is acyl.
4. The method of claim 1, wherein R is monophosphate.
5. The method of claim 1, wherein R is diphosphate.
6. The method of claim 1, wherein R is triphosphate.
7. The method of claim 1, wherein R is a stabilized phosphate derivative.

8. A method for the treatment of hepatitis B virus infection in a host comprising administering an effective amount of a β-L-(3'-azido)-2',3'-dideoxy-5-fluorocytidine of the formula:

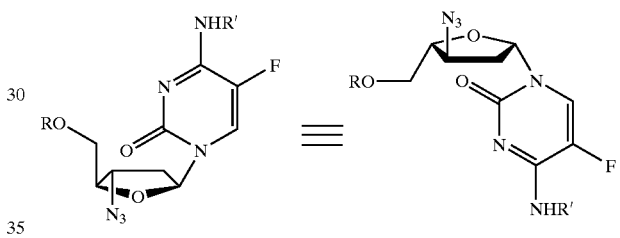

or a pharmaceutically acceptable ester, salt or prodrug thereof, wherein R is H, acyl, monophosphate, diphosphate, or triphosphate, or a stabilized phosphate derivative (to form a stabilized nucleotide prodrug), R' is H, acyl, or alkyl.

9. The method of claim 8, wherein R is H.
10. The method of claim 8, wherein R is acyl.
11. The method of claim 8, wherein R is monophosphate.
12. The method of claim 8, wherein R is diphosphate.
13. The method of claim 8, wherein R is triphosphate.
14. The method of claim 8, wherein R is a stabilized phosphate derivative.

15. A β-L-(2'-azido)-2',3'-dideoxy-5-fluorocytidine of the formula:

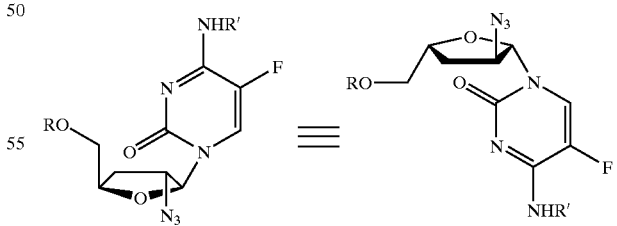

or a pharmaceutically acceptable ester, salt or prodrug thereof, wherein R is H, acyl, monophosphate, diphosphate, or triphosphate, or a stabilized phosphate derivative (to form a stabilized nucleotide prodrug), and R' is H, acyl, or alkyl.

16. The compound of claim 15, wherein R is H.
17. The compound of claim 15, wherein R is acyl.
18. The compound of claim 15, wherein R is monophosphate.

19. The compound of claim 15, wherein R is diphosphate.

20. The compound of claim 15, wherein R is triphosphate.

21. The compound of claim 15, wherein R is a stabilized phosphate derivative.

22. A β-L-(3'-azido)-2',3'-dideoxy-5-fluorocytidine of the formula:

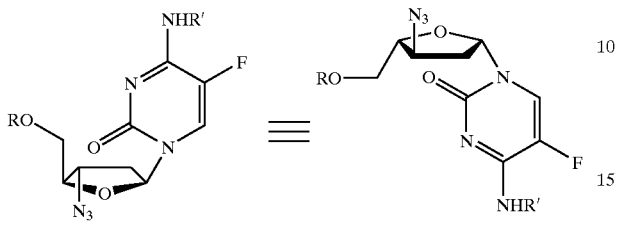

or a pharmaceutically acceptable ester, salt or prodrug thereof, wherein R is H, acyl, monophosphate, diphosphate, or triphosphate, or a stabilized phosphate derivative (to form a stabilized nucleotide prodrug), R' is H, acyl, or alkyl.

23. The compound of claim 22, wherein R is H.

24. The compound of claim 22, wherein R is acyl.

25. The compound of claim 22, wherein R is monophosphate.

26. The compound of claim 22, wherein R is diphosphate.

27. The compound of claim 22, wherein R is triphosphate.

28. The compound of claim 22, wherein R is a stabilized phosphate derivative.

29. A pharmaceutical composition for the treatment of hepatitis B virus infection in a host comprising an effective amount of a β-L-(2'-azido)-2',3'-dideoxy-5-fluorocytidine of the formula:

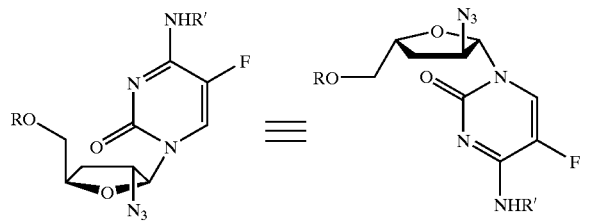

or a pharmaceutically acceptable ester, salt or prodrug thereof, wherein R is H, acyl, monophosphate, diphosphate, or triphosphate, or a stabilized phosphate derivative (to form a stabilized nucleotide prodrug), and R' is H, acyl, or alkyl.

30. The composition of claim 29, wherein R is H.

31. The composition of claim 29, wherein R is acyl.

32. The composition of claim 29, wherein R is monophosphate.

33. The composition of claim 29, wherein R is diphosphate.

34. The composition of claim 29, wherein R is triphosphate.

35. The composition of claim 29, wherein R is a stabilized phosphate derivative.

36. A pharmaceutical composition for the treatment of hepatitis B virus infection in a host comprising an effective amount of a β-L-(3'-azido)-2',3'-dideoxy-5-fluorocytidine of the formula:

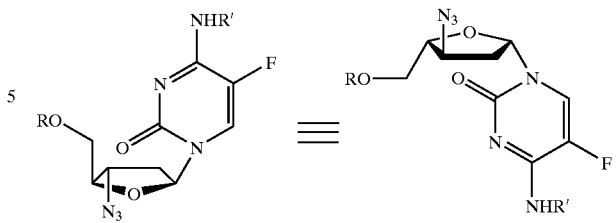

or a pharmaceutically acceptable ester, salt or prodrug thereof, wherein R is H, acyl, monophosphate, diphosphate, or triphosphate, or a stabilized phosphate derivative (to form a stabilized nucleotide prodrug), R' is H, acyl, or alkyl.

37. The composition of claim 36, wherein R is H.

38. The composition of claim 36, wherein R is acyl.

39. The composition of claim 36, wherein R is monophosphate.

40. The composition of claim 36, wherein R is diphosphate.

41. The composition of claim 36, wherein R is triphosphate.

42. The composition of claim 36, wherein R is a stabilized phosphate derivative.

43. A method for the treatment of hepatitis B virus infection in a host comprising administering an effective amount of a β-L-(2'-azido)-2',3'-dideoxy-5-fluorocytidine of the formula:

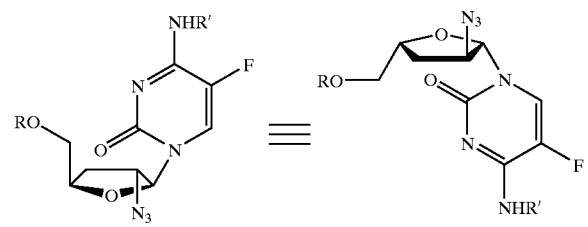

or a pharmaceutically acceptable salt thereof, wherein R is H, acyl, monophosphate, diphosphate or triphosphate, and R' is H, acyl or alkyl.

44. A method for the treatment of hepatitis B virus infection in a host comprising administering an effective amount of a β-L-(3'-azido)-2',3'-dideoxy-5-fluorocytidine of the formula:

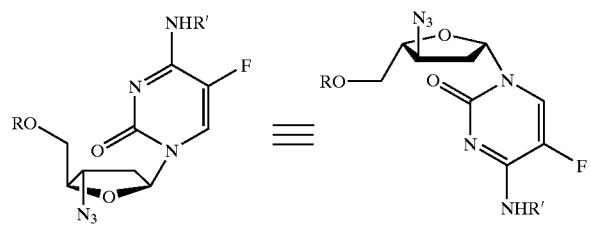

or a pharmaceutically acceptable salt thereof, wherein R is H, acyl, monophosphate, diphosphate or triphosphate, and R' is H, acyl or alkyl.

45. The method of claim 43 or 44, wherein R is H and R' is H.

46. The method of claim 43 or 44, wherein R is acyl and R' is H.

47. The method of claim 43 or 44, wherein R is monophosphate and R' is H.

48. The method of claim 43 or 44, wherein R is diphosphate and R' is H.

49. The method of claim 43 or 44, wherein R is triphosphate and R' is H.
50. The method of claim 43 or 44, wherein R is H and R' is alkyl.
51. The method of claim 43 or 44, wherein R is acyl and R' is alkyl.
52. The method of claim 43 or 44, wherein R is monophosphate and R' is alkyl.
53. The method of claim 43 or 44, wherein R is diphosphate and R' is alkyl.
54. The method of claim 43 or 44, wherein R is triphosphate and R' is alkyl.
55. The method of claim 43 or 44, wherein R is H and R' is acyl.
56. The method of claim 43 or 44, wherein R is acyl and R' is acyl.
57. The method of claim 43 or 44, wherein R is monophosphate and R' is acyl.
58. The method of claim 43 or 44, wherein R is diphosphate and R' is acyl.
59. The method of claim 43 or 44, wherein R is triphosphate and R' is acyl.
60. The method of any one of claims 43–59, wherein the host is a human.
61. The method of any one of claims 43–59, wherein the host is a non-human animal.
62. A β-L-(2'-azido)-2',3'-dideoxy-5-fluorocytidine of the formula:

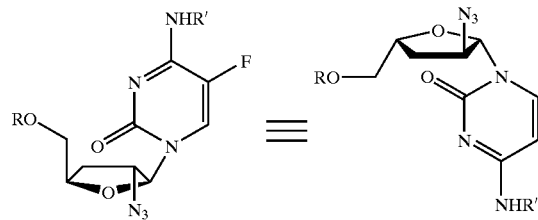

or a pharmaceutically acceptable salt thereof, wherein R is H, acyl, monophosphate, diphosphate or triphosphate, and R' is H, acyl or alkyl.
63. A β-L-(3'-azido)-2',3'-dideoxy-5-fluorocytidine of the formula:

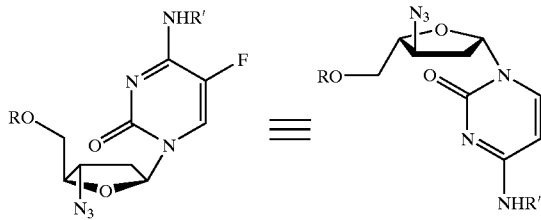

or a pharmaceutically acceptable ester, salt or prodrug thereof, wherein R is H, acyl, monophosphate, diphosphate or triphosphate,an R' is H, acyl or alkyl.
64. The compound of claim 62 or 63, wherein R is H and R' is H.
65. The compound of claim 62 or 63, wherein R is acyl and R' is H.
66. The compound of claim 62 or 63, wherein R is monophosphate and R' is H.
67. The compound of claim 62 or 63, wherein R is diphosphate and R' is H.
68. The compound of claim 62 or 63, wherein R is triphosphate and R' is H.
69. The compound of claim 62 or 63, wherein R is H and R' is alkyl.
70. The compound of claim 62 or 62, wherein R is acyl and R' is alkyl.
71. The compound of claim 62 or 63, wherein R is monophosphate and R' is alkyl.
72. The compound of claim 62 or 63, wherein R is diphosphate and R' is alkyl.
73. The compound of claim 62 or 63, wherein R is triphosphate and R' is alkyl.
74. The compound of claim 62 or 63, wherein R is H and R' is acyl.
75. The compound of claim 62 or 63, wherein R is acyl and R' is acyl.
76. The compound of claim 62 or 63, wherein R is monophosphate and R' is acyl.
77. The compound of claim 62 or 63, wherein R is diphosphate and R' is acyl.
78. The compound of claim 62 or 63, wherein R is triphosphate and R' is acyl.
79. A pharmaceutical composition for the treatment of hepatitis B virus infection in a host comprising an effective amount of a β-L-(2'-azido)-2',3'-dideoxy-5-fluorocytidine of the formula:

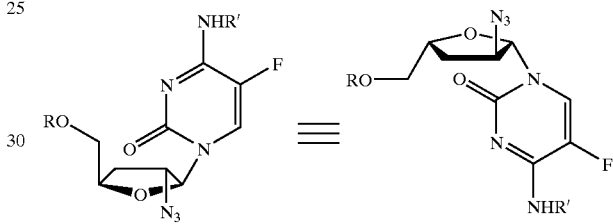

or a pharmaceutically acceptable ester, salt or prodrug thereof, wherein R is H, acyl, monophosphate, diphosphate or triphosphate, and R' is H, acyl or alkyl.
80. A pharmaceutical composition for the treatment of hepatitis B virus infection in a host comprising an effective amount of a β-L-(3'-azido)-2',3'-dideoxy-5-fluorocytidine of the formula:

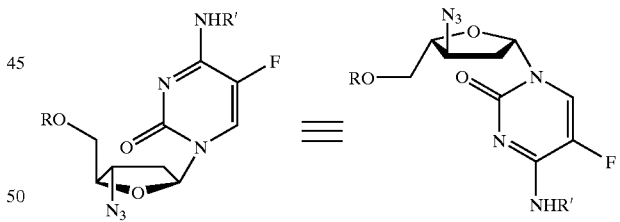

or a pharmaceutically acceptable ester, salt or prodrug thereof, wherein R is H, acyl, monophosphate, diphosphate or triphosphate, R' is H, acyl or alkyl.
81. The composition of claim 79 or 80, wherein R is H and R' is H.
82. The composition of claim 79 or 80, wherein R is acyl and R' is H.
83. The composition of claim 79 or 80, wherein R is monophosphate and R' is H.
84. The composition of claim 79 or 80, wherein R is diphosphate and R' is H.
85. The composition of claim 79 or 80, wherein R is triphosphate and R' is H.
86. The composition of claim 79 or 80, wherein R is H and R' is alkyl.

87. The composition of claim 79 or 80, wherein R is acyl and R' is alkyl.

88. The composition of claim 79 or 80, wherein R is monophosphate and R' is alkyl.

89. The composition of claim 79 or 80, wherein R is diphosphate and R' is alkyl.

90. The composition of claim 79 or 80, wherein R is triphosphate and R' is alkyl.

91. The composition of claim 79 or 80, wherein R is H and R' is acyl.

92. The composition of claim 79 or 80, wherein R is acyl and R' is acyl.

93. The composition of claim 79 or 80, wherein R is monophosphate and R' is acyl.

94. The composition of claim 79 or 80, wherein R is diphosphate and R' is acyl.

95. The composition of claim 79 or 80, wherein R is triphosphate and R' is acyl.

96. The composition of any one of claims 79–95, wherein the host is a human.

97. The method of any one of claims 79–95, wherein the host is a non-human animal.

* * * * *